(12) United States Patent
Jewett et al.

(10) Patent No.: US 10,457,932 B2
(45) Date of Patent: Oct. 29, 2019

(54) METHODS FOR IN VITRO RIBOSOME SYNTHESIS AND EVOLUTION

(71) Applicant: Northwestern University, Evanston, IL (US)

(72) Inventors: Michael Christopher Jewett, Evanston, IL (US); Brian R. Fritz, Chicago, IL (US)

(73) Assignee: Northwestern University, Evanston, IL (US)

( * ) Notice: Subject to any disclaimer, the term of this patent is extended or adjusted under 35 U.S.C. 154(b) by 175 days.

(21) Appl. No.: 15/639,401

(22) Filed: Jun. 30, 2017

(65) Prior Publication Data

US 2017/0306320 A1    Oct. 26, 2017

Related U.S. Application Data

(63) Continuation-in-part of application No. PCT/IB2015/059964, filed on Dec. 23, 2015.

(60) Provisional application No. 62/098,622, filed on Dec. 31, 2014.

(51) Int. Cl.
*C40B 30/04* (2006.01)
*C12N 15/10* (2006.01)

(52) U.S. Cl.
CPC ..... *C12N 15/1058* (2013.01); *C12N 15/1041* (2013.01); *C40B 30/04* (2013.01)

(58) Field of Classification Search
None
See application file for complete search history.

(56) References Cited

PUBLICATIONS

Stemmer, W.P. (1994) Rapid evolution of a protein in vitro by DNA shuffling. Nature, 370, 389-391.
Takahashi, F., Ebihara, T., Mie, M., Yanagida, Y., Endo, Y., Kobatake, E. and Aizawa, M. (2002) Ribosome display for selection of active dihydrofolate reductase mutants using immobilized methotrexate on agarose beads. FEBS Lett., 514, 106-110.
Talkington, M.W., Siuzdak, G. and Williamson, J.R. (2005) An assembly landscape for the 30S ribosomal subunit. Nature, 438, 628-632.
Terasaka, N., Hayashi, G., Katoh, T. and Suga, H. (2014) An orthogonal ribosome-tRNA pair via engineering of the peptidyl transferase center. Nat. Chem. Biol., 10, 555-557.
Traub, P. and Nomura, M. (1968) Structure and function of E. coli ribosomes. V. Reconstitution of functionally active 30S ribosomal particles from RNA and proteins. Proc. Natl. Acad. Sci. U. S. A., 59, 777-784.
Wang, K., Neumann, H., Peak-Chew, S.Y. and Chin, J.W. (2007) Evolved orthogonal ribosomes enhance the efficiency of synthetic genetic code expansion. Nat. Biotechnol., 25, 770-777.
Youngman, E.M. and Green, R. (2005) Affinity purification of in vivo-assembled ribosomes for in vitro biochemical analysis. Methods, 36, 305-312.

(Continued)

*Primary Examiner* — Christian C Boesen
(74) *Attorney, Agent, or Firm* — Quarles & Brady LLP; M. Scott McBride

(57) ABSTRACT

Disclosed are methods, components, compositions, and kits for preparing and identifying engineered *E. coli* ribosomes. The *E. coli* ribosomes may be prepared and identified under a set of defined conditions, such as in the presences of antibiotics, in order to obtain an engineered ribosome that is resistant to the antibiotic.

15 Claims, 11 Drawing Sheets

Specification includes a Sequence Listing.

(56) References Cited

PUBLICATIONS

Zahnd C. Amstutz, P. and Pluckthun, A. (2007) Ribosome display: selecting and evolving proteins in vitro that specifically bind to a target. Nat. Methods, 4, 269-279.
International Search Report for PCT/IB2015/059946 dated Apr. 8, 2016.
Written Opinion for PCT/IB2015/059946 dated Apr. 8, 2016.
International Preliminary Report on Patentability for PCT/IB2015/059964 dated Jul. 13, 2017.
Baneyx, F. (1999) Recombinant protein expression in *Escherichia coli*. Curr. Opin. Biotechnol., 10, 411-421.
Binz, H.K., Amstutz, P., Kohl, A., Stumpp, M.T., Briand, C., Forrer, P., Gruffer, M.G. and Pluckthun, A. (2004) High-affinity binders selected from designed ankyrin repeat protein libraries. Nat. Biotechnol., 22, 575-582.
Bremer, H. and Dennis, P.P. (1996) Modulation of Chemical Composition and Other Parameters of the Cell by Growth Rate. In Neidhardt, F. C., Curtiss III, R., Ingraham, J. L., Lin, E. C. C., Low, K. B., Magasanik, B., Reznikoff, W. S. and Riley, M. (eds.), *Escherichia coli* and *Salmonella*: Cellular and Molecular Biology. 2nd ed. American Society for Microbiology, Washington, DC., pp. 1553-1569.
Cadwell, R.C. and Joyce, G.F. (1994) Mutagenic PCR. PCR Methods Appl., 3, S136-140.
Cannone, J.J., Subramanian, S., Schnare, M.N., Collett, J.R., D'Souza, L.M., Du, Y., Feng, B., Lin, N., Madabusi, L.V., Muller, K.M. et al. (2002) The comparative RNA web (CRW) site: an online database of comparative sequence and structure information for ribosomal, intron, and other RNAs. BMC Bioinf., 3, 2.
Carlson, E.D., Gan, R., Hodgman, C.E and Jewett, M.C. (2012) Cell-free protein synthesis: applications come of age. Biotechnol. Adv., 30, 1185-1194.
Chou, C.P. (2007) Engineering cell physiology to enhance recombinant protein production in *Escherichia coli*. Appl. Microbiol. Biotechnol., 76, 521-532.
Cirino, P.C., Mayer, K.M. and Umeno, D. (2003) Generating mutant libraries using error-prone PCR. Methods Mol. Biol., 231, 3-9.
Cochella, L. and Green, R. (2004) Isolation of antibiotic resistance mutations in the rRNA by using an in vitro selection system. Proc. Nal Acad. Sci. U. S. A., 101, 3786-3791.
Engler, C., Kandzia, R. and Marillonnet, S. (2008) A one pot, one step, precision cloning method with high throughput capability. PLoS One, 3, e3647.
Evans, M.S., Ugrinov, K.G., Frese, M.A. and Clark, P.L. (2005) Homogeneous stalled ribosome nascent chain complexes produced in vivo or in vitro. Nat. Methods, 2, 757-762.
Fritz, B.R., Jamil, O.K. and Jewett, M.C. (2014) Implications of macromolecular crowding and reducing conditions for in vitro ribosome construction. In preparation.
Fritz, B.R. and Jewett, M.C. (2014) The impact of transcriptional tuning on in vitro integrated rRNA transcription and ribosome construction. Nucleic Acids Res., 42, 6774-6785.
Gibson, D.G., Young, L., Chuang, R.Y., Venter, J.C., Hutchison, C.A., 3rd and Smith, H.O. (2009) Enzymatic assembly of DNA molecules up to several hundred kilobases. Nat Methods, 6, 343-345.
Green, R. and Noller, H.F. (1996) In vitro complementation analysis localizes 23S rRNA posttranscriptional modifications that are required for *Escherichia coli* 50S ribosomal subunit assembly and function. RNA, 2, 1011-1021.
Green, R. and Noller, H.F. (1999) Reconstitution of functional 50S ribosomes from in vitro transcripts of Bacillus stearothermophilus 23S rRNA. Biochemistry, 38, 1772-1779.
Hanes, J. and Pluckthun, A. (1997) In vitro selection and evolution of functional proteins by using ribosome display. Proc. Natl. Acad. Sci, U. S. A., 94, 4937-4942.

Hanes, J., Schaffitzel, C., Knappik, A. and Pluckthun, A. (2000) Picomolar affinity antibodies from a fully synthetic naive library selected and evolved by ribosome display. Nat. Biotechnol., 18, 1287-1292.
Herold, M. and Nierhaus, K.H. (1987) Incorporation of six additional proteins to complete the assembly map of the 50 S subunit from *Escherichia coli* ribosomes. J. Biol. Chem., 262, 8826-8833.
Hodgman, C.E. and Jewett, M.G. (2012) Cell-free synthetic biology: thinking outside the cell. Metab. Eng., 14, 261-269.
Hui, A. and de Boer, H.A. (1987) Specialized ribosome system: preferential translation of a single mRNA species by a subpopulation of mutated ribosomes in *Escherichia coli*. Proc. Natl. Acad. Sci. U. S. A., 84, 4762-4766.
Jewett, M.C. and Swartz, J.R. (2004) Mimicking the *Escherichia coli* cytoplasmic environment activates long-lived and efficient cell-free protein synthesis. Biotechnol. Bioeng., 86, 19-26.
Jewett, M.C., Fritz, B.R., Timmerman, L.E. and Church, G.M. (2013) In vitro integration of ribosomal RNA synthesis, ribosome assembly, and translation. Mol. Syst. Biol., 9, 678.
Katzen, F. Chang, G. and Kudlicki, W. (2005) The past, present and future of cell-free protein synthesis. Trends Biotechnol., 23, 150-156.
Keiler, K.C., Waller, P.R. and Sauer, R.T. (1996) Role of a peptide tagging system in degradation of proteins synthesized from damaged messenger RNA. Science, 271, 990-993.
Kim, D.M., Kigawa, T., Choi, C.Y. and Yokoyama, S. (1996) A highly efficient cell-free protein synthesis system from *Escherichia coli*. Eur. J. Biochem., 239, 881-886.
Lamla, T. and Erdmann, V.A. (2001) In vitro selection of other proteins than antibodies by means of ribosome display. FEBS Lett., 502, 35-40.
Lee, K., Varma, S. SantaLucia, J., Jr. and Cunningham, P.R. (1997) In vivo determination of RNA structure-function relationships: analysis of the 790 loop in ribosomal RNA. J. Mol. Biol., 269, 732-743.
Liu, Y., Fritz, B.R., Anderson, M.J., Schoborg, J.A. and Jewett, M.C. (2014) Characterizing and Alleviating Substrate Limitations for Improved in vitro Ribosome Construction. ACS Synth. Biol.
Matsuura, T. and Pluckthun, A. (2003) Selection based on the folding properties of proteins with ribosome display. FEBS Lett., 539, 24-28.
Mizushima, S. and Nomura, M. (1970) Assembly mapping of 30S ribosomal proteins from *E. coli*. Nature, 226, 1214.
Nakatogawa, H. and Ito, K. (2002) The ribosomal exit tunnel functions as a discriminating gate. Cell, 108, 629-636.
Neumann, H., Wang, K., Davis, L., Garcia-Alai, M. and Chin, J.W. (2010) Encoding multiple unnatural amino acids via evolution of a quadruplet-decoding ribosome. Nature, 464, 441-444.
Neylon, C. (2004) Chemical and biochemical strategies for the randomization of protein encoding DNA sequences: library construction methods for directed evolution. Nucleic Acids Res., 32, 1448-1459.
Nierhaus, K.H. and Dohme, F. (1974) Total reconstitution of functionally active 50S ribosomal subunits from *Escherichia coli*. Proc. Natl. Acad. Sci. U. S. A., 71, 4713-4717.
Ohashi, H., Shimizu, Y., Ying, B.W. and Ueda, T. (2007) Efficient protein selection based on ribosome display system with purified components. Biochem. Biophys. Res. Commun., 352, 270-276.
Ohta, A., Yamagishi, Y. and Suga, H. (2008) Synthesis of biopolymers using genetic code reprogramming. Curr. Opin. Chem. Biol., 12, 159-167.
Parker, J. (1989) Errors and alternatives in reading the universal genetic code. Microbiol. Rev., 53, 273-298.
Pluckthun, A. (2012) Ribosome display: a perspective. Methods Mol. Biol., 805, 3-28.
Polacek, N., Gaynor, M., Yassin, A. and Mankin, A.S. (2001) Ribosomal peptidyl transferase can withstand mutations at the putative catalytic nucleotide. Nature, 411, 498-501.
Quan, J. and Tian, J. (2009) Circular polymerase extension cloning of complex gene libraries and pathways. PLoS One, 4, e6441.
Rackham, O. and Chin, J.W. (2005) A network of orthogonal ribosome x mRNA pairs. Nat. Chem. Biol., 1, 159-166.

(56) References Cited

PUBLICATIONS

Rackham, O. and Chin, J.W. (2005) Cellular logic with orthogonal ribosomes. J. Am. Chem. Soc., 127, 17584-17585.

Roberts, R.W. (1999) Totally in vitro protein selection using mRNA-protein fusions and ribosome display. Curr. Opin. Chem. Biol., 3, 268-273.

Rozen, S. and Skaletsky, H. (2000) Primer3 on the WWW for general users and for biologist programmers. Methods Mol. Biol., 132, 365-386.

Schaffitzel, C., Hanes, J., Jermutus, L. and Pluckthun, A. (1999) Ribosome display: an in vitro method for selection and evolution of antibodies from libraries. J. Immunol. Methods, 231, 119-135.

Schlunzen, F., Zarivach, R., Harms, J., Bashan, A., Tocilj, A., Albrecht, R., Yonath, A. and Franceschi, F. (2001) Structural basis for the interaction of antibiotics with the peptidyl transferase centre in eubacteria. Nature, 413, 814-821.

Semrad, K. and Green, R. (2002) Osmolytes stimulate the reconstitution of functional 50S ribosomes from in vitro transcripts of *Escherichia coli* 23S rRNA. RNA, 8, 401-411.

Sorensen, H.P. and Mortensen, K.K. (2005) Advanced genetic strategies for recombinant protein expression in *Escherichia coli*. J. Biotechnol., 115, 113-128.

Stemmer, W.P. (1994) DNA shuffling by random fragmentation and reassembly: in vitro recombination for molecular evolution. Proc. Natl. Acad. Sci. U. S. A., 91, 10747-10751.

METHODS FOR IN VITRO RIBOSOME SYNTHESIS AND EVOLUTION

CROSS-REFERENCE TO RELATED PATENT APPLICATIONS

The present application is a continuation-in-part of International Application No. PCT/IB2015/059964, filed on Dec. 23, 2015, published on Jul. 7, 2016 as WO 2016/108159, which claims the benefit of priority under 35 U.S.C. § 119(e) to U.S. Provisional Patent Application No. 62/098,622, filed on Dec. 31, 2014, the contents of which are incorporated herein by reference in their entireties.

STATEMENT REGARDING FEDERALLY SPONSORED RESEARCH OR DEVELOPMENT

This invention was made with government support under GM081450 awarded by the National Institutes of Health; W911NF-11-1-0445 awarded by the Army Research Office; MCB0943383 awarded by the National Science Foundation; and N00014-11-1-0363 awarded by the Office of Naval Research. The government has certain rights in the invention.

BACKGROUND

The present invention generally relates to methods for in vitro synthesis of ribosomes. More specifically, the present invention relates to methods of synthesizing, evolving, and screening ribosomes for variants.

*Escherichia coli* ribosomes are capable of polymerizing amino acids into complex polypeptides with diverse functions. To engineer or modify ribosomes, we have previously reported on the integrated synthesis, assembly, and translation (iSAT) system, in which ribosomal RNA (rRNA) can be in vitro transcribed and assembled into functional ribosomes. Here we report the coupling of the iSAT system with ribosome display, a method for stalling ribosomes, to create the ribosome synthesis and evolution (RISE) method. RISE uses mutated DNA to build a library of ribosomes that can then be screened for functionality under different conditions. With our optimized protocol, we observe >1,000-fold specificity for functional ribosomes, which allows for rapid screening of large libraries of rRNA mutations. As a demonstration, we used RISE to explore mutations of the ribosomal peptidyl transferase center, and found RISE rapidly converged libraries of 4,096 and $1.7 \times 10^7$ sequences back to the wild type sequence. Additionally, we evolved resistance to the antibiotic clindamycin and uncovered novel resistant combinations of base mutations. Moving forward, RISE will serve as a powerful new approach for exploring the effects of rRNA mutations on ribosome function and to ultimately isolate ribosomal variants with altered functionalities.

The applications of the disclosed methods include in vitro study of ribosome biogenesis; ribosome evolution for ribosome engineering or modification; encapsulation within emulsions for compartmentalized ribosome evolution; rapid, high-throughput testing of new antibiotics against ribosome assembly; antibiotic discovery; and minimal cells. Furthermore, the disclosed methods enable the ability to repurpose the translational apparatus by evolving ribosomes to synthesize sequence-controlled polymers containing D-α-amino acids, β- and γ-amino acids, and, most ambitiously, polyketides. This achievement will ultimately allow the template-guided biosynthesis and evolution of sequence-controlled peptide mimetics, polyketides, fatty acids, and ever more complex molecules that combine these disparate functional units. Additionally, the disclosed methods enable evolution of ribosomes to produce new types of sequence-defined polymers that include: new catalytic triads; unique metal site; protease resistance in peptides and proteins; libraries of mixed peptide.PK hybrids; and libraries of mixed peptide.NP conjugates. Further, one could use the disclosed methods to test and engineer and/or modify the ribosome to produce polymers based on novel poly-condensation chemistries.

The advantages of the disclosed methods are several. The disclosed methods improve upon existing ribosome engineering and modifying approaches by using a wholly in vitro ribosome evolution method. This is the first method to our knowledge that allows for whole 70S ribosome evolution without dominant lethal constraints. The disclosed ribosome evolution method shows greater than 1,000-fold specificity for functional ribosomes under different conditions. The in vitro ribosome evolution method allows for rapid probing of viability of rRNA sequence modifications. It could also allow researchers to understand the fundamental constraints for engineering and modifying the RNA based active site of the ribosome and the polymer excretion tunnel.

The method of ribosome engineering and modifying outlined herein is of great interest to the fields of biotechnology, chemistry, and material science. Previous approaches have depended on in vivo ribosome biogenesis. Yet in vivo ribosome biogenesis is limited by cell viability restrictions and transformation efficiency and requires purification of the ribosomes from cell lysates. The development of an in vitro ribosome biogenesis technology removes these limitations and expands the possibilities of ribosome engineering and modification. Ribosomes may be engineered and/or modified to incorporate unnatural amino acids for expanded protein functionality or to perform new chemistry for the production of non-protein polymers.

The disclosed methods modify iSAT technology to combine it with ribosome display to enable ribosome evolution. This may allow us to identify new methods for inhibiting the ribosome to lead to new antibiotics. In addition, evolved ribosomes may be able to synthesize sequence-controlled polymers containing D-α-amino acids, β- and γ-amino acids, and, most ambitiously, polyketides. This achievement will ultimately allow the template-guided biosynthesis and evolution of sequence-controlled peptide mimetics, polyketides, fatty acids, and ever more complex molecules that combine these disparate functional units. Further, it will allow the manufacture of polymers based on alternative poly-condensation chemistries (i.e., non amide bonds).

SUMMARY

Disclosed are methods, components, compositions, and kits for preparing and identifying engineered and/or modified *E. coli* ribosomes. The *E. coli* ribosomes may be prepared and identified under a set of defined conditions.

The disclosed methods include methods of identifying an engineered and/or modified *E. coli* ribosome having functional activity under a defined condition. The methods may include: (a) performing an integrated ribosome synthesis assembly and translation (iSAT) reaction with a library of mutated rRNA templates and a ribosome display reporter template; and (b) partitioning a subpopulation of rRNAs in assembled mutated ribosomes having translational activity under the defined condition from a remainder population of mutated rRNAs present in the iSAT reaction; and (c) enriching the partitioned subpopulation of rRNAs in assembled mutated ribosomes having translational activity to identify the engineered and/or modified *E. coli* ribosome having functional activity under the defined condition. Optionally, the methods may include generating the library of mutated rRNA templates. The disclosed methods may include methods of identifying an engineered and/or modified *E. coli* ribosome having functional activity in the presence of an antibiotic. As such, engineered and/or modified *E. coli* ribosomes also are contemplated herein.

Also disclosed are components and compositions, for example, components and compositions for performing the disclosed methods. The disclosed components may include polynucleotides for performing the disclosed methods such as ribosome display vectors. The ribosome display vectors may include: (a) a reporter gene encoding at least the beginning of an open reading frame; (b) a promoter element operably linked to the 5' end of the reporter gene and configured to transcribe mRNA encoding the reporter gene; (c) a spacer element operably linked to the 3' end of the reporter gene and lacking a stop codon in frame with the open reading frame of the reporter gene; and (d) a self-cleaving ribozyme element operably linked 3' to the spacer element and configured to generate a run-off transcript comprising the open reading frame of the reporter gene.

Also disclosed are kits. The disclosed kits may include one or more components for performing any of the disclosed methods. The kits may include ribosome display vectors as disclosed herein.

DETAILED DESCRIPTION

Definitions and Terminology

Figure 1:
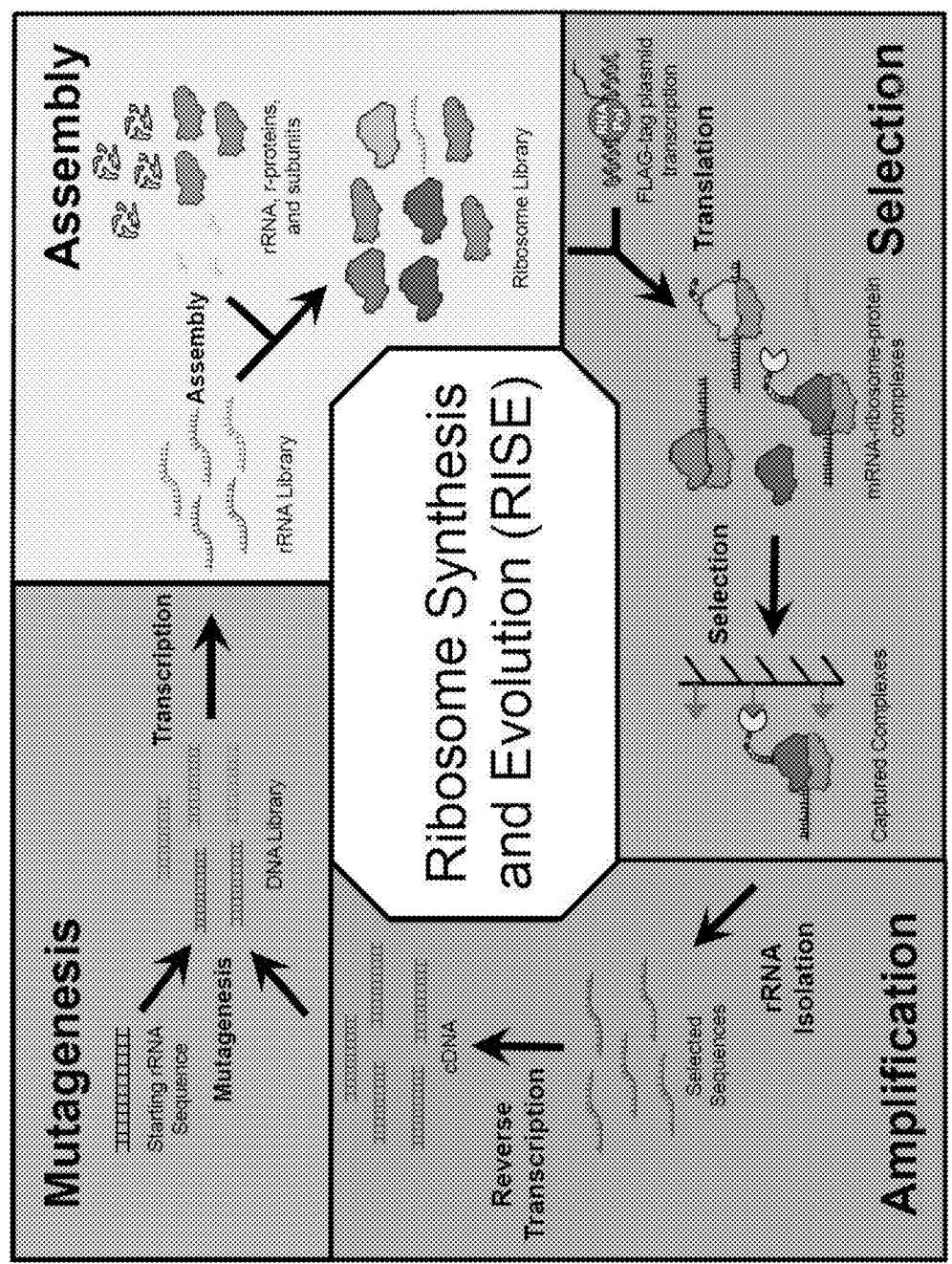
FIG. 1. Diagram of ribosome synthesis and evolution (RISE) method.

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a tRNA" should be interpreted to mean "one or more tRNAs" unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into subranges as discussed above.

A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

Polynucleotides and Synthesis Methods

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present methods, an oligonucleotide also can comprise nucleotide analogs in which the base, sugar, or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Letters* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference.

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The terms "target," "target sequence", "target region", and "target nucleic acid," as used herein, are synonymous and refer to a region or sequence of a nucleic acid which is to be amplified, sequenced, or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, N.Y.; Wetmur, 1991, Critical Review in Biochem. and Mol. Biol. 26(3/4):227-259; and Owczarzy et al., 2008, *Biochemistry,* 47: 5336-5353, which are incorporated herein by reference).

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)$_n$ sequence, where n is in the range from about 20 to about 200). The region of the primer that is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

The term "promoter" refers to a cis-acting DNA sequence that directs RNA polymerase and other trans-acting transcription factors to initiate RNA transcription from the DNA template that includes the cis-acting DNA sequence.

As used herein, the term "sequence defined biopolymer" refers to a biopolymer having a specific primary sequence. A sequence defined biopolymer can be equivalent to a genetically-encoded defined biopolymer in cases where a gene encodes the biopolymer having a specific primary sequence.

As used herein, "expression template" refers to a nucleic acid that serves as substrate for transcribing at least one RNA that can be translated into a sequence defined biopolymer (e.g., a polypeptide or protein). Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

In certain exemplary embodiments, vectors such as, for example, expression vectors, containing a nucleic acid encoding one or more rRNAs or reporter polypeptides and/or proteins described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Such vectors are referred to herein as "expression vectors." In general, expression vectors of utility in recombinant DNA techniques are often in the form of plasmids. In the present specification, "plasmid" and "vector" can be used interchangeably. However, the disclosed methods and compositions are intended to include such other forms of expression vectors, such as viral vectors (e.g., replication defective retroviruses, adenoviruses and adeno-associated viruses), which serve equivalent functions.

In certain exemplary embodiments, the recombinant expression vectors comprise a nucleic acid sequence (e.g., a nucleic acid sequence encoding one or more rRNAs or reporter polypeptides and/or proteins described herein) in a form suitable for expression of the nucleic acid sequence in one or more of the methods described herein, which means that the recombinant expression vectors include one or more regulatory sequences which is operatively linked to the nucleic acid sequence to be expressed. Within a recombinant expression vector, "operably linked" is intended to mean that the nucleotide sequence encoding one or more rRNAs or reporter polypeptides and/or proteins described herein is linked to the regulatory sequence(s) in a manner which allows for expression of the nucleotide sequence (e.g., in an in vitro ribosomal assembly, transcription and/or translation system). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990).

Oligonucleotides and polynucleotides may optionally include one or more non-standard nucleotide(s), nucleotide analog(s) and/or modified nucleotides. Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

Peptides, Polypeptides, Proteins, and Synthesis Methods

As used herein, the terms "peptide," "polypeptide," and "protein," refer to molecules comprising a chain a polymer of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include nonstandard, noncanonical, or unnatural amino acids, which optionally may include amino acids other than any of the following amino acids: alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine residues. The term "amino acid residue" may include alpha-, beta-, gamma-, and delta-amino acids.

In some embodiments, the term "amino acid residue" may include nonstandard, noncanonical, or unnatural amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. The term "amino acid residue" may include L isomers or D isomers of any of the aforementioned amino acids.

Other examples of nonstandard, noncanonical, or unnatural amino acids include, but are not limited, to a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GlcNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenyl-alanine, a p-amino-L-phenylalanine, an isopropyl-L-phenyl-alanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, 15ufa15hor, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α,α disubstituted amino acid; a β-amino acid; a γ-amino acid, a cyclic amino acid other than proline or histidine, and an aromatic amino acid other than phenylalanine, tyrosine or tryptophan.

As used herein, a "peptide" is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length >100 amino acids (Garrett & Grisham, Biochemistry, $2^{nd}$ edition, 1999, Brooks/Cole, 110). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues.

A peptide as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

The disclosed platforms may be utilized to evolve ribosomes that can be used to mediate polymerization of amino acid monomers and/or non-amino acid monomers. Non-amino acid monomers that may be subjected to ribosome-mediated polymerization include, but are not limited to: polyester monomers, polyaramid monomers, polyurethane monomers, polyketide monomers, polyolefin monomers, polycarbonate monomers, polyethylene monomers, polypropylene monomers, coumarin monomers, phenylene monomers, and vinylene monomers among others. Preferably, the disclosed evolved ribosomes may be utilized to mediate polymerization of a range of "A|B"-type monomers which form complementary nucleophilic and electrophilic monomer pairs for polymerization.

As used herein, "translation template" refers to an RNA product of transcription from an expression template that can be used by ribosomes to synthesize polypeptides or proteins.

The term "reaction mixture," as used herein, refers to a solution containing reagents necessary to carry out a given reaction. A reaction mixture is referred to as complete if it contains all reagents necessary to perform the reaction. Components for a reaction mixture may be stored separately in separate container, each containing one or more of the total components. Components may be packaged separately for commercialization and useful commercial kits may contain one or more of the reaction components for a reaction mixture.

The steps of the methods described herein can be performed in any suitable order unless otherwise indicated herein or otherwise clearly contradicted by context. The steps may be repeated or reiterated any number of times to achieve a desired goal unless otherwise indicated herein or otherwise clearly contradicted by context.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Ribosome Synthesis

Methods for making ribosomes have been disclosed in published U.S. patent applications, e.g., U.S. Published Application No. 2012-017120, the content of which is incorporated herein by reference in its entirety. Methods for making ribosomes have been described in scientific publications, e.g., Fritz et al., "Implications of macromolecular crowding and reducing conditions for in vitro ribosome construction," Nucl. Acids. Res. 2015 May 19; 43(9):4774-84; Liu et al., "Characterizing and alleviating substrate limitations for improved in vitro ribosome construction," ACS Synth. Biol. 2015 Apr. 17; 4(4):454-62; Fritz and Jewett, "The impact of transcriptional tuning on in vitro integrated rRNA transcription and ribosome construction," Nucl. Acids Res. 2014 June; 42(10):6774-85; and Jewett et al., "In vitro integration of ribosomal RNA synthesis, ribosome assembly, and translation," Mol. Syst. Biol. 2013 Jun. 25; 9:678; the contents of which are incorporated herein by reference in their entireties.

The methods disclosed herein include methods of reconstituting a functional translation unit. In certain aspects, the reconstituted ribosomes described herein can synthesize a reporter. Furthermore, active E. coli ribosomes can be reconstituted in a one-step incubation procedure at 37° C. under conditions that mimic the cytoplasm. In vitro transcribed 16S rRNA and 23S rRNA, may be combined with native ribosomal proteins and native 5S rRNA in order to self-assemble functional synthetic ribosomes.

In some embodiments, compositions for rRNA synthesis, ribosome assembly and protein synthesis in one vessel are provided. The reconstitution methods described herein facilitate the in vitro analysis of ribosomal mutations for understanding the molecular details of ribosome function. The reconstitution methods described herein enable cell-free synthetic biology as a platform for evolving ribosomes for the production of protein therapeutics and peptide drugs that are difficult to make in vivo.

In some embodiments, methods for making an in vitro assembled ribosomal subunit and/or ribosome are provided. In certain aspects, a modular, step-wise approach is provided in which in vivo purified portions of ribosomes and/or in vitro produced purified portions of ribosomes can be used to make natural ribosomes or ribosomal subunits, semi-synthetic ribosomes or ribosomal subunits (i.e., portions are in vivo purified and portions are in vitro produced (i.e., by in vitro transcription and/or in vitro translation)) as well as fully synthetic ribosomes or ribosomal subunits (i.e., the entire ribosome or ribosomal subunit is made up of portions that were in vitro produced (i.e., by in vitro transcription and/or in vitro translation)). As used herein, a portion of a ribosome refers to a polypeptide, a ribosomal subunit or an rRNA that can be used to produce a ribosome. Proteins and/or polypeptides produced by in vitro translation may be referred to as "synthetic proteins" and "synthetic polypeptides," respectively. In vitro transcribed rRNA is referred to herein as "synthetic rRNA."

In certain aspects, ribosomal subunit assembly and/or ribosome assembly and in vitro rRNA transcription are performed in the same vessel, optionally concomitantly. In other aspects, ribosomal subunit assembly and/or ribosome assembly and in vitro translation are performed in the same vessel optionally concomitantly. In still other aspects, ribosomal subunit assembly and/or ribosome assembly, in vitro rRNA transcription, and in vitro translation are performed in the same vessel optionally concomitantly.

In certain exemplary embodiments, one or more of the methods described herein are performed in a vessel, e.g., a single, vessel. The term "vessel," as used herein, refers to any container suitable for holding on or more of the reactants (e.g., for use in one or more transcription, ribosomal subunit/ribosome assembly, and/or translation steps) described herein. Examples of vessels include, but are not limited to, a microtitre plate, a test tube, a microfuge tube, a beaker, a flask, a multi-well plate, a cuvette, a flow system, a microfiber, a microscope slide and the like.

In certain exemplary embodiments, physiologically compatible (but not necessarily natural) ions and buffers are utilized for coupled ribosome assembly and translation, e.g., potassium glutamate, ammonium chloride and the like. Ribosomal subunits are reconstituted in physiological conditions (e.g., constant temperature and magnesium). Using cytoplasmic mimicry as a guide, salt conditions are provided as well as salts themselves in which ribosomal subunits are reconstituted. Physiological cytoplasmic salt conditions are well-known to those of skill in the art.

In certain exemplary embodiments, methods for the in vitro assembly of ribosomes and/or ribosomal subunits are provided. As used herein, the term assemble refers to the ability of portions of ribosomes to interact with one another. As used herein, the terms "bind," "binding," "interact," "interacting," "occupy" and "occupying" refer to covalent interactions, noncovalent interactions and steric interactions. A covalent interaction is a chemical linkage between two atoms or radicals formed by the sharing of a pair of electrons (a single bond), two pairs of electrons (a double bond) or three pairs of electrons (a triple bond). Covalent interactions are also known in the art as electron pair interactions or electron pair bonds. Noncovalent interactions include, but are not limited to, van der Waals interactions, hydrogen bonds, weak chemical bonds (via short-range noncovalent forces), hydrophobic interactions, ionic bonds and the like. A review of noncovalent interactions can be found in Alberts et al., in Molecular Biology of the Cell, 3d edition, Garland Publishing, 1994. Steric interactions are generally understood to include those where the structure of the compound is such that it is capable of occupying a site by virtue of its three dimensional structure, as opposed to any attractive forces between the compound and the site.

In certain exemplary embodiments, one or more reporter polypeptides and/or proteins are utilized as a read-out to assay ribosomal subunit and/or ribosome activity (i.e., the ability of the ribosomal subunit and/or ribosome to mediate translation). In certain aspects, the polypeptide and/or protein contains a detectable label. In other aspects, the reporter polypeptide and/or protein provides a biological activity (e.g., an enzymatic activity, bioluminescence, fluorescence or the like) that serves as a detectable label.

Examples of fluorescent proteins include, but are not limited to, yellow fluorescent protein (YFP), green fluorescence protein (GFP), cyan fluorescent protein (CFP), umbelliferone, fluorescein, fluorescein isothiocyanate, rhodamine, dichlorotriazinylamine fluorescein, dansyl chloride, phycoerythrin and the like. Examples of bioluminescent markers include, but are not limited to, luciferase (e.g., bacterial, firefly, click beetle and the like), luciferin, aequorin and the like. Examples of enzyme systems having visually detectable signals include, but are not limited to, galactosidases, glucorinidases, phosphatases, peroxidases, cholinesterases and the like.

Methods for In Vitro Ribosome Synthesis and Evolution

The present inventors have invented methods, components, compositions, and kits for preparing and identifying engineered and/or modified E. coli ribosomes. The E. coli ribosomes may be prepared and identified under a set of defined conditions.

In a first aspect, a method of identifying an engineered and/or modified E. coli ribosome having functional activity under a defined condition is described. The method may include the following steps: (a) performing an integrated ribosome synthesis assembly and translation (iSAT) reaction (e.g., as disclosed herein) with a library of mutated rRNA templates (e.g., as disclosed herein) and a ribosome display reporter template (e.g., as disclosed herein); and (b) partitioning a subpopulation of rRNAs in assembled mutated ribosomes having translational activity under the defined condition from a remainder population of mutated rRNAs present in the iSAT reaction; and (c) enriching the partitioned subpopulation of rRNAs in assembled mutated ribosomes having translational activity to identify the engineered and/or modified E. coli ribosome having functional activity under the defined condition. In the disclosed methods, the steps (a)-(c) may be executed in a reiterative manner.

Optionally, the method includes a step whereby a library of mutated rRNA templates is generated prior to performing the method. In some embodiments, the library of mutated rRNA templates is generated by a method that includes a step selected from the group consisting of DNA shuffling, error-prone DNA amplification, degenerate primer-based DNA amplification, and specific modifications based on crystal structure guided rational targeting. The library may include members representing one of four different nucleotides at one or more variable positions in the rRNA, wherein $4^N$ represents the theoretical number of different members in the library and N represents the number of variable positions.

The disclosed methods may utilize a ribosome display reporter template. The ribosome display reporter template may be transcribed from a plasmid vector such as the vectors described herein. The plasmid vector may include a reporter gene operably linked to a 5'-promoter element, a 3'-spacer element, and a 3'-self-cleaving ribozyme element. As such, from 5' →3', the vector may include 5'-promoter element→reporter gene→3'-spacer element→3'-self-cleaving ribozyme element.

The reporter gene utilized in the disclosed methods may encode a binding partner as disclosed herein, and the disclosed methods may include a partitioning step that utilizes the binding partner. In some embodiments, the partitioning step may include: (i) forming a ternary complex comprising a stalled ribosome on a mRNA terminated by a self-cleaving ribozyme in the presence of an anti-ssrA oligonucleotide; and (ii) selecting the ternary complex with a cognate binding partner to the binding partner encoded by the reporter gene to form a quaternary complex comprising the ternary complex associated with the cognate binding partner. The cognate binding partner to the binding partner encoded by the reporter gene may comprise a capture reagent. For example, the binding partner encoded by the reporter gene may comprise a peptide tag that is captured by the cognate binding partner. Optionally, the cognate binding partner may be conjugated to a solid support, such as a resin in a column, in order to capture the complex. Suitable tags may include, but are not limited to a FLAG-tag, a 3×FLAG-tag, a His-tag, a Strep-tag, and a glutathione S-transferase tag. After the complex is bound by the cognate binding partner (e.g., which optionally is bound to a solid support such as a column resin), the complex may be washed in order to purify the complex and identify the ribosome associated with the complex.

The disclosed methods typically include an enriching step. The enriching step may include (i) recovering a subpopulation of rRNAs in assembled mutated ribosomes having translational activity (e.g., as obtained through the aforementioned partitioning step); (ii) converting the subpopulation of rRNAs to form a plurality of rRNA templates; and (iii) amplifying the plurality of rRNA templates (e.g., via performing RT-PCR). The amplified plurality of rRNA templates may be utilized to generate a new library of mutated rRNA templates for the disclosed methods. The steps of the disclosed methods (i.e., steps (a)-(c) as aforementioned) may be executed in a reiterative manner, for example, to simulate evolution of the library of mutated rRNA templates and converge the mutated rRNA templates.

The disclosed methods may be performed under a defined condition. For example, the methods may be performed under a defined condition in order to select for ribosomes that are translationally active under the defined condition. Suitable defined conditions may include, but are not limited to, a defined temperature or temperature range, a defined pH or pH range, a redox environment, or the presence of one or more additives (e.g., one or more antibiotics, in order to identify ribosomes that are translationally active in the present of the antibiotic, and hence, resistant to the antibiotic).

In a second aspect, components and compositions are disclosed, for example, components and compositions for performing the disclosed methods. The disclosed components and compositions may include polynucleotides, such as polynucleotide vectors such as ribosome display vectors. In some embodiments, the ribosome display vectors include: (a) a reporter gene encoding at least the beginning of an open reading frame (i.e., at least the 5' end of an open reading frame); (b) a promoter element operably linked to the 5' end of the reporter gene and configured to transcribe mRNA encoding the reporter gene; (c) a spacer element operably linked to the 3' end of the reporter gene and lacking a stop codon in frame with the open reading frame of the reporter gene; and (d) a self-cleaving ribozyme element operably linked 3' to the spacer element and configured to generate a run-off transcript comprising the open reading frame of the reporter gene. As such, the ribosome display vector may include, reading from 5' →3', as follows: 5'-promoter element→reporter gene→3'-spacer element→3'-self-cleaving ribozyme element.

The 3' spacer element typically has a length that is sufficient to provide for a ribosome exit tunnel. For example, the 3'-spacer element may be at least 10, 15, 20, 25, 30, 35, 40, 45, 50 nucleotides or longer.

The 3'-self-cleaving ribozyme element typically cleaves the nascent RNA and generates a run-off transcript. In some embodiments, the self-cleaving ribozyme element comprises a hammerhead self-cleaving ribozyme.

The ribosome display vector typically includes a reporter gene encoding a reporter molecule. The reporter gene may encode at least a portion of a binding partner. For example, the reporter gene may encode at least a portion of a binding partner encoded in frame with the beginning of the open reading frame of the reporter gene. Suitable binding partners may include peptide tags (e.g., a FLAG-tag, a 3×FLAG-tag, a His-tag, a Strep-tag, and a glutathione S-transferase tag).

In a third aspect, methods for identifying an engineered and/or modified *E. coli* ribosome having functional activity in the presence of an antibiotic. The methods may include the following steps: (a) performing an integrated ribosome synthesis assembly and translation (iSAT) reaction (e.g., as disclosed herein) with a library of mutated rRNA templates (e.g., as disclosed herein) and a ribosome display reporter template (e.g., as disclosed herein) in the presence of an antibiotic; and (b) partitioning a subpopulation of rRNAs in assembled mutated ribosomes having translational activity in the presence of the antibiotic from a remainder population of mutated rRNAs present in the iSAT reaction; and (c) enriching the partitioned subpopulation of rRNAs in assembled mutated ribosomes having translational activity in the presence of the antibiotic to identify the engineered and/or modified *E. coli* ribosome having functional activity in the presence of the antibiotic. In the disclosed methods, the steps (a)-(c) may be executed in a reiterative manner. Suitable antibiotics for the disclosed methods may include any antibiotic that inhibits translation, and in particular, ribosomal activity associated required for translation. Suitable antibiotics may include, but are not limited to clindamycin.

In a fourth aspect, an antibiotic-resistant ribosome is described. The antibiotic-resistant ribosome includes a product produced by the aforementioned methods for identifying an engineered and/or modified *E. coli* ribosome having functional activity in the presence of an antibiotic.

In a fifth aspect, kits comprising one or more components for performing the aforementioned methods are disclosed. The kits may comprise one or more components for performing an iSAT reaction as disclosed herein. The kits may comprise one or more components for performing RISE reaction as disclosed herein. For example, the disclosed kits may comprising one ore more components including a ribosome display vector as disclosed herein.

The methods and/or compositions disclosed herein may be practiced and/or prepared by practicing and/or modifying methods and compositions in the art. (See, e.g., Fritz et al., "Implications of macromolecular crowding and reducing conditions for in vitro ribosome construction," Nucl. Acids Res. 2015 May 19; 43(9):4774-84; Liu et al., "Characterizing and alleviating substrate limitations for improved in vitro ribosome constructions," ACS Synth. Biol. 2015 Apr. 17; 4(4):454-62; Fritz et al., "The impact of transcriptional tuning on in vitro integrated rRNA transcription and ribosome construction," Nucl Acids Res. 2014 June; 42(10): 6774-85; Jewett et al., "In vitro integration of ribosomal RNA synthesis, ribosome assembly, and translation," Mol Syst Biol. 2013 Jun. 25; 9:678; and Fritz et al., "Biology by design: from top to bottom and back," J Biomed Biotechnol. 2010; 2010:232016; the contents of which are incorporated herein by reference in their entireties).

ILLUSTRATIVE EMBODIMENTS

The following embodiments are illustrative and are not intended to limit the scope of the claimed subject matter.

Embodiment 1

A method of identifying an engineered and/or modified *E. coli* ribosome having functional activity under a defined condition, comprising: (a) performing an integrated ribosome synthesis assembly and translation (iSAT) reaction with a library of mutated rRNA templates and a ribosome display reporter template; and (b) partitioning a subpopulation of rRNAs in assembled mutated ribosomes having translational activity under the defined condition from a remainder population of mutated rRNAs present in the iSAT reaction; and (c) enriching the partitioned subpopulation of rRNAs in assembled mutated ribosomes having translational activity to identify the engineered and/or modified E. coli ribosome having functional activity under the defined condition.

Embodiment 2

The method of embodiment 1, further comprising generating the library of mutated rRNA templates.

Embodiment 3

The method of embodiment 2, wherein the library of mutated rRNA templates is generated by a method that includes a step selected from the group consisting of DNA shuffling, error-prone DNA amplification, degenerate primer-based DNA amplification, and specific modifications based on crystal structure guided rational targeting.

Embodiment 4

The method of any of the foregoing embodiments, wherein the ribosome display reporter template comprises a reporter gene operably linked to a 5'-promoter element, a 3'-spacer element, and a 3'-self-cleaving ribozyme element.

Embodiment 5

The method of embodiment 4, wherein the reporter gene comprises or encodes a binding partner.

Embodiment 6

The method of embodiment 5, wherein the partitioning step (b) comprises: (i) forming a ternary complex comprising a stalled ribosome on a mRNA terminated by a self-cleaving ribozyme in the presence of an anti-ssrA oligonucleotide; and (ii) selecting the ternary complex with a cognate binding partner to the binding partner of the reporter gene to form a quaternary complex comprising the ternary complex associated with the cognate binding partner.

Embodiment 7

The method of embodiment 6, wherein the cognate binding partner comprises a capture reagent.

Embodiment 8

The method of embodiment 6, wherein the binding partner encoded by the reporter gene comprises or encodes a peptide tag.

Embodiment 9

The method of embodiment 8, wherein the peptide tag is selected from a group consisting of FLAG-tag, 3×FLAG-tag, His-tag, Strep-tag, and glutathione S-transferase.

Embodiment 10

The method of embodiment 9, further comprising washing the selected quaternary complex under a defined stringency condition.

Embodiment 11

The method of embodiment 1, wherein the enriching step (c) comprises: (i) recovering the subpopulation of rRNAs in assembled mutated ribosomes having translational activity; (ii) converting the subpopulation of rRNAs to form a plurality of rRNA templates; and (iii) amplifying the plurality of rRNA templates.

Embodiment 12

The method of any of the foregoing embodiments, wherein the defined condition is selected from the group consisting of defined temperature, defined pH, a redox environment, or the presence of one or more additives.

Embodiment 13

The method of embodiment 12, wherein the one or more additives comprise an antibiotic.

Embodiment 14

The method of any of the foregoing embodiments, further comprising executing steps (a)-(c) in a reiterative manner.

Embodiment 15

A ribosome display vector comprising: (a) a reporter gene encoding the beginning of an open reading frame; (b) a promoter element operably linked to the 5' end of the reporter gene and configured to transcribe mRNA encoding the reporter gene; (c) a spacer element operably linked to the 3' end of the reporter gene and lacking a stop codon in frame with the open reading frame of the reporter gene; and (d) a self-cleaving ribozyme element operably linked 3' to the spacer element and configured to generate a run-off transcript comprising the open reading frame of the reporter gene.

Embodiment 16

The ribosome display vector of embodiment 15, wherein the 3' spacer element comprises a sufficient length to provide for a ribosome exit tunnel.

Embodiment 17

The ribosome display vector of embodiment 15, wherein the self-cleaving ribozyme element comprises a hammerhead self-cleaving ribozyme.

Embodiment 18

The ribosome display vector of embodiment 15, wherein the reporter gene further comprises a binding partner encoded in frame with the beginning of the open reading frame of the reporter gene.

Embodiment 19

The ribosome display vector of embodiment 18, wherein the binding partner comprises a peptide tag.

Embodiment 20

The ribosome display vector of embodiment 19, wherein the peptide tag is selected from a group consisting of FLAG-tag, 3×FLAG-tag, His-tag, Strep-tag, and glutathione S-transferase.

Embodiment 21

A method of identifying an engineered and/or modified E. coli ribosome having functional activity in the presence of an antibiotic, the method comprising performing the method of any of embodiments 1-14 in the presence of the antibiotic.

Embodiment 22

The method of embodiment 20, wherein the antibiotic comprises clindamycin.

Embodiment 23

An antibiotic-resistant ribosome comprising a product produced by the method of embodiment 21.

Embodiment 24

A kit comprising any or all of the components utilized in the methods of embodiments 1-14.

Embodiment 25

A kit comprising the ribosome display vector of any of embodiments 15-20.

Embodiment 26

A kit comprising any or all of the components utilized in the methods of embodiments 21-23.

EXAMPLES

The following Examples are illustrative and are not intended to limit the scope of the claimed subject matter.

In Vitro Ribosome Synthesis and Evolution Through Ribosome Display

Abstract

*Escherichia coli* ribosomes have been the subject of extensive genetic, structural, and functional studies, as they are capable of polymerizing amino acids into complex polypeptides with diverse biological functions. The synthesis capability of *E. coli* ribosomes has been harnessed through recombinant protein synthesis, though efforts to alter the function of ribosomes have been limited due to cell viability restrictions in vivo. However, we have recently reported on the in vitro construction of *E. coli* ribosomes through the integrated synthesis, assembly, and translation (iSAT) system, in which ribosomal RNA (rRNA) can be transcribed and assembled into functional ribosomes in a single isothermal reaction. Here we report the coupling of the iSAT system with ribosome display, a method of stalling ribosomes during translation after expression of a selective peptide or protein, to create the ribosome synthesis and evolution (RISE) method. RISE uses mutated DNA to transcribe a library of rRNA that is then assembled into a library of ribosomes. Functional ribosomes are isolated from the library using ribosome display selection. After thorough optimization of the RISE system, we observe >1,000-fold specificity for functional ribosomes, which would allow for screening of $10^9$ rRNA sequences in just three rounds of selection. This specificity is on par with other highly efficient ribosome display systems. As a demonstration, we used RISE to explore the viability of mutations of the peptidyl transferase center of the *E. coli* ribosome, and found RISE rapidly converged libraries of 4,096 and 1.7× $10^7$ sequences back to the wild type sequence. This result suggests that the bases we mutated were not amenable to alternate sequences and demonstrates the efficiency of RISE in practice. To demonstrate ribosome engineering with RISE, we evolved resistance to the antibiotic clindamycin and uncovered novel resistant combinations of base mutations. Moving forward, RISE will serve as a powerful new approach for exploring the effects of rRNA mutations on ribosome function and to ultimately isolate ribosomal variants with altered functionalities

INTRODUCTION

The *E. coli* ribosome is a powerful macromolecular machine capable of sequence-defined polymerization of 20 amino acid monomers at a rate of up to 21 amino acids per sec (1) and an error rate of approximately 1 in 10,000 (2). Researchers have sought to harness this ability for decades, with the field of recombinant protein synthesis emerging as a means to utilize native ribosomes in living cells (3-5). Further, the field of the cell-free protein synthesis has emerged in recent years to liberate ribosomes from cell viability constraints and allow for easier manipulation of the translation reaction (6-10).

Beyond native ribosomes, researchers have sought to engineer ribosomes to introduce new functions such as non-natural amino acid incorporation through genetic code expansion (11-13). One approach has utilized ribosome variants that have a modified anti-Shine Dalgarno region of 16S ribosomal RNA (rRNA) of the small subunit to create a subset of orthogonal ribosomes within *E. coli* cells that translate unique mRNA while not interfering with native translation (14-16). These ribosomes have been used to study the effects of mutations on 16S rRNA (17) as well as create ribosomes with improved ability to incorporate unnatural amino acids (12,13). While this approach is limited to mutations of the 16S rRNA, mutations of the 23S rRNA of the large subunit can be studied through the purification of in vivo constructed ribosome variants through inclusion of an MS2 tag in the 23S rRNA sequence (18-20). However, efforts to engineer ribosomes in vivo are limited by cell viability and transformation restrictions (18), as particular ribosome variants can lead to lethality through interference with native ribosomes.

To overcome limitations of in vivo ribosome engineering, we developed the integrated synthesis, assembly, and translation (iSAT) system, in which ribosomal RNA (rRNA) is synthesized, assembled with purified native proteins into ribosomes, and assayed for activity through the translation of a reporter protein (21-24). The most significant contribution of the iSAT system is the coupled transcription and assembly of rRNA into complete functional 70S ribosomes, as previous efforts focused on either the small 30S subunit (25-27) or the large 50S subunit only (28-31), and efforts to incorporate in vitro transcribed 23S rRNA failed to yield highly functional particles, likely due to the lack of post-transcriptional modifications (31,32). Meanwhile, the iSAT system is able to construct 70S *E. coli* ribosomes from synthetic rRNA with activity approximately 70% that of native *E. coli* ribosomes (21).

With the iSAT system working at high efficiency, we next sought to develop a ribosome engineering method by combining iSAT with a method for screening functional variants under different conditions. We were inspired by ribosome display, as it is a method used in protein engineering to complex mRNA, ribosomes, and peptides through ribosome stalling (33-36). Cochella and Green demonstrated that ribosome display can be used for the selection of functional ribosomes from amongst a ribosome library, but their method required in vivo ribosome synthesis and ribosome purification, and the method required six cycles to screen a library of 4,096 sequences (18). We believed that the iSAT system would be capable of screening larger libraries with much greater efficiency and prevent sequence bias that can occur from transformation and in vivo ribosome synthesis.

For ribosome display, one translation stalling mechanism uses mRNA without a stop codon. Translating ribosomes will stall at the end of such a message, and a native mechanism for dissociating stalled ribosomes utilizing a transfer-messenger RNA (tmRNA), known as ssrA, can be blocked by including an anti-ssrA oligonucleotide in the reaction mixture. (33,37). For protein engineering, mRNA is transcribed from a library of DNA sequences that can be generated by a variety of DNA mutagenesis strategies, PCR with degenerate primers (42), and specific modifications based on crystal structure guided rational targeting. The DNA library is followed by a spacer sequence to account for the length of the ribosomal exit tunnel. Upon translation and stalling, the complexes include a library of exposed peptides translated from the library of mRNA. The peptide library can then be screened for novel activities, such as target affinity (43,44), protein folding (45), enzyme activity (46). By complexing the mRNA, ribosome, and peptide, selection of the peptide also selects for the mRNA that encoded it. Selected mRNA can be recovered and analyzed or used for subsequent cycles to converge the library to the most highly selected sequences.

For ribosome engineering, we developed ribosome display to work with the in vitro iSAT system, but instead of generating a library of mRNA species, we sought to transcribe a library of rRNA that could then be assembled into a library of ribosomes. By using the library of ribosomes to express a selective tag and then selecting for that tag, we would select for ribosomes that had demonstrated functionality. The rRNA of the functional ribosomes could then be isolated, analyzed, and reassembled into operons for subsequent cycles of ribosome display. Such a system could be used for evolving ribosomes to function under different conditions, such as temperature, pH, or redox environment, or in the presence of particular additives, such as antibiotics.

Here we report the development and demonstration of our ribosome synthesis and evolution (RISE) method that combines the iSAT system with ribosome display (FIG. 1). RISE was been tuned for high specificity of functional ribosomes over non-specific binding of ribosomes or ribosomal components, allowing for rapid screening of rRNA mutation libraries. For demonstration of the RISE system, we first applied it to libraries of novel mutations in the peptidyl transferase center of ribosomes to test our ability to manipulate the catalytic core of the ribosome. Then, we compared RISE to the previous study of Cochella and Green where in vivo constructed ribosomes were evolved to function in the presence of the antibiotic clindamycin. The results presented here reveals the vast potential of RISE to allow for improved understanding of the E. coli ribosome through exploration of rRNA sequence manipulation and directed evolution of ribosomes for altered functionalities.

Materials and Methods

Plasmid and Library Construction.

The plasmids pT7rrnB (containing rRNA operon rrnB) and the reporter plasmids pK7LUC and pY71sfGFP were used in iSAT reactions as previously described (22,23). A variant of pT7rrnB with a 660 bp deletion in the 23S gene was created by inverse PCR as previously described (22).

Plasmids for ribosome display were developed starting from the pRDV plasmid (47,48). For selective peptide or protein gene insertion, the gene was first amplified by PCR with primers encoding a 5'-GGTGGT-3' spacer and restriction sites for either NcoI for forward primers or BamHI for reverse primers. The amplified genes and pRDV were digested with NcoI and BamHI and the correct fragments were isolated by gel electrophoresis and extracted. Fragments were ligated with Quick Ligase (NEB) and transformed into heat shock competent DH5α cells, plated, and grown overnight. Resulting isolated colonies were grown for plasmid purification and sequencing.

Libraries of rRNA operons were created from the pT7rrnB plasmid through PCR amplification of particular rRNA gene fragments with phosphorylated primers containing overhangs of degenerate bases. DNA fragments were ligated and PCR amplified for in vitro insertion into the pT7rrnB plasmid (see below), iSAT Reaction.

iSAT reactions were performed as previously described (21,22). Briefly, salts, substrates, and cofactors were mixed with 1 to 4 nM reporter plasmid and a molar equivalent of pT7rrnB or 8-fold excess of in vitro assembled rRNA operon plasmid libraries (see below). For ribosome display reactions, the anti-ssrA oligonucleotide (5'-TTAAGCT-GCTAAAGCGTAGTTTTCGTCGTTTGCGACTA-3' (SEQ ID NO:1)) was included at 5 µM to prevent dissociation of stalled ribosomes. Then a mix of proteins were added to final concentrations of approximately 2 mg/mL S150 extract, 300 nM total protein of the 70S ribosome (TP70), and 60 µg/mL T7 RNA polymerase. Reactions were mixed gently by pipetting and incubated at 37° C. Preparation of S150 extract, TP70, and T7 RNA polymerase have been previously described (21-23). For sfGFP production, quantification was performed as previously described (22).

Sedimentation Analysis.

Sedimentation analysis was performed as previously described (21). Briefly, ribosome profiles were determined from 50 µL iSAT reactions by incubating reactions for 2 h at 37° C., loading them onto a 10-40% sucrose gradient made with Buffer C (10 mM Tris-OAc (pH=7.5 at 4° C.), 60 mM $NH_4Cl$, 7.5 mM $Mg(OAc)_2$, 0.5 mM EDTA, 2 mM DTT) and ultra-centrifuging the reactions for 35,000 rpm for 18 h at 4° C. Gradients were then analyzed through spectrophotometry and fractionation (500 µL fractions). Ribosome profiles were generated from absorbance of the gradient at 254 nm and peaks were determined from comparison to previous traces (21).

Ribosome Synthesis and Evolution (RISE).

For RISE, 15 µL iSAT reactions were performed as described above, including the anti-ssrA oligonucleotide. Reactions were incubated at 37° C. for 15 min to 2 h (see text). At completion, reactions were placed at 4° C. and diluted with 4 volumes (60 µL) of binding buffer (50 mM Tris-acetate (pH 7.5 at 4° C.), 50 mM magnesium acetate, 150 mM NaCl, 1% Tween® 20, and 0.0 to 5.0% bovine serum albumin (BSA) or 0 to 20 mg/mL heparin). Meanwhile, for each reaction, 10 µL packed gel volume of magnetic bead with selective marker or antibody were washed three times with 50 µL bead wash buffer (50 mM Tris-acetate (pH 7.5 at 4° C.), 50 mM magnesium acetate, 150 mM NaCl). Diluted iSAT reactions were added to washed beads and incubated at 4° C. for 1 h with gentle rotation to suspend beads in solution. Reactions were then washed five or ten times with wash buffer (50 mM Tris-acetate (pH 7.5 at 4° C.), 50 mM magnesium acetate, 150 to 1000 mM NaCl, and 0.05 to 5% Tween® 20), with 5 or 15 min incubations of each wash step at 4° C. Wash buffer was removed from the beads and 50 µL elution buffer (50 mM Tris-acetate (pH 7.5 at 4° C.), 150 mM NaCl, 50 mM EDTA (Ambion)) was added, and the beads were incubated at 4° C.

for 30 min with gentle rotation. Elution buffer was recovered from beads for rRNA analysis and/or amplification.

Reverse Transcription Polymerase Chain Reaction (RT-PCR).

Figure 11:
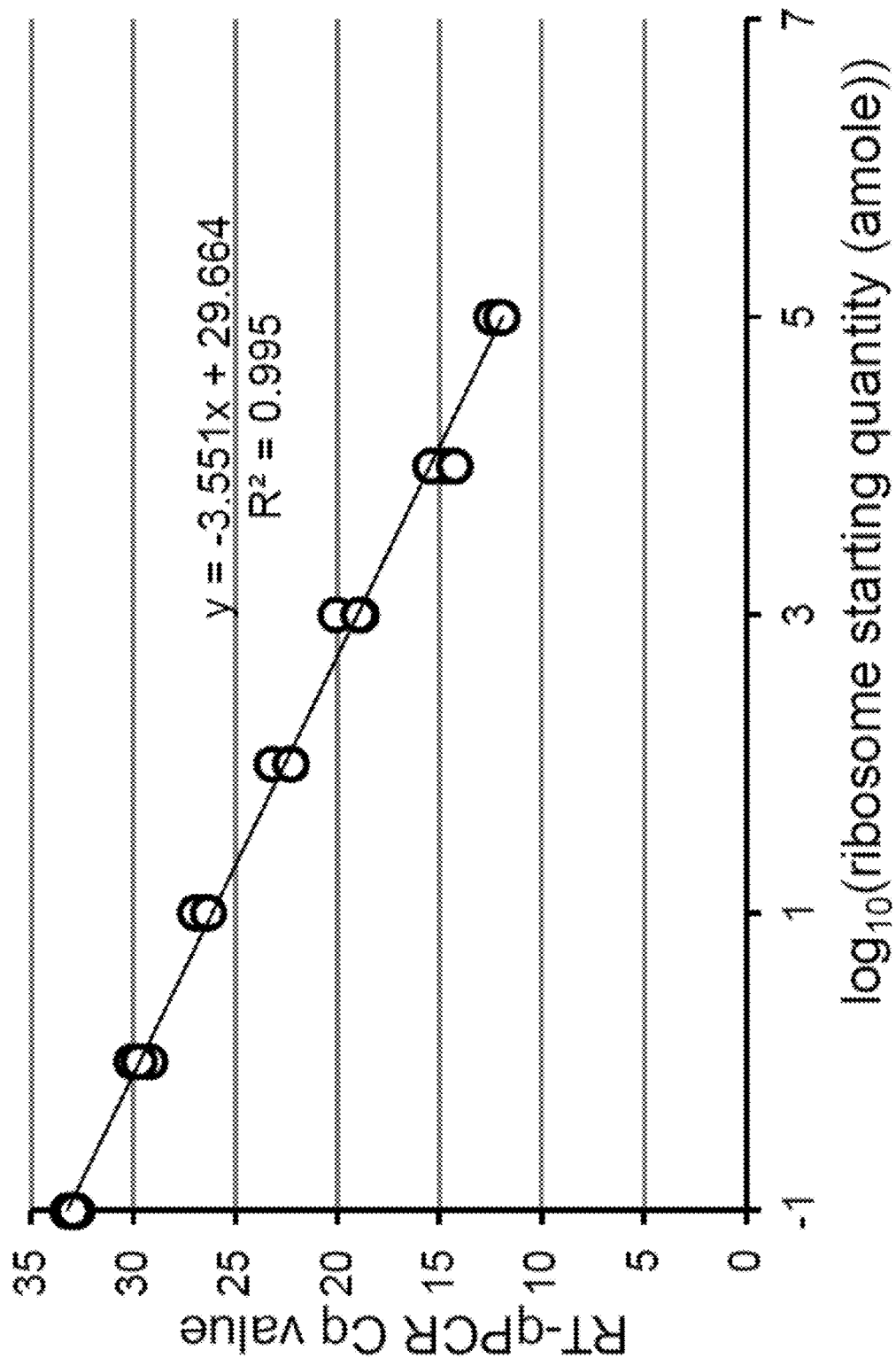
FIG. 11. 23S rRNA RT-qPCR standard curve for dilution series of purified 70S *E. coli* ribosomes (NEB).

For quantitative RT-PCR of 23S rRNA, RNA recovered from ribosome display was diluted 1:100 with nuclease-free water to dilute EDTA in the elution buffer. Diluted samples were used with the iTaq™ Universal SYBR® Green One-Step Kit (Bio-Rad) in 10 µL reactions following product literature. For quantitation, primers were designed for amplification of 23S rRNA using Primer3 software (49). Reactions were monitored for fluorescence in a CFX96™ Real-Time PCR Detection System (Bio-Rad). A standard curve was generated from a dilution series of 70S E. coli ribosomes (NEB) to ensure linearity of the assay FIG. 11.

For recovery of rRNA from ribosome display, rRNA recovered from ribosome display was purified with the RNeasy MinElute Cleanup Kit (Qiagen) and eluted with 14 µL nuclease-free water. Purified rRNA was used with the SuperScript® III One-Step RT-PCR System with Platinum® Taq DNA Polymerase (Invitrogen™) in 30 µL reactions following product literature. Primers were designed for use in both 23S rRNA recovery and in vitro operon plasmid assembly (see below).

In Vitro Operon Plasmid Assembly.

For library construction or rRNA recovery, PCR was performed using Phusion polymerase with primers that amplify the bases 1962 to 2575 of the 23S rRNA gene. The primers also included unique cut sites for the off-site type IIs restriction enzyme SapI, such that the approximately 660 bp fragments and pT7rrnBΔ660 were digested with SapI in 1× CutSmart™ buffer (NEB) for 2 h at 37° C. DNA was purified and inserts and plasmid were ligated at a 1:1 molar ratio with Quick Ligase (NEB) for 20 min at room temperature. The resulting plasmids were purified with DNA Clean & Concentrator-5™ (Zymo Research), eluted with nuclease-free water, and analyzed by NanoDrop to determine concentration.

Results

Ribosome Display Reporter Plasmid Development.

While protein engineering for ribosome display utilizes mRNA libraries that are unique for each protein target, the RISE approach utilizes a single mRNA species encoding a selective peptide tag and spacer sequence. To generate large quantities of a single mRNA, we sought to develop a plasmid construct that would allow for in vitro transcription within the iSAT reaction. The key consideration for this selective tag plasmid design was the need to remove any stop codon at the 3' end of the mRNA to preserve the stalling mechanism of ribosome display.

To design our selective reporter, we started with a ribosome display vector, pRDV, developed for protein engineering efforts (47,48). This construct includes a T7 promoter, two multiple cloning sites for gene insertion and a TolA spacer sequence. The pRDV plasmid was intended for PCR reactions to generate template for mRNA run-off transcription. However, since our current iSAT system does not tolerate liner DNA templates, we modified the pRDV vector to ensure removal of stop codons from our mRNA by introducing a self-cleaving hammerhead (HH) ribozyme gene after the spacer sequence. Upon transcription, the self-cleaving ribozyme would process the 3' end of mRNA to ensure removal of stop codons.

Figure 2:
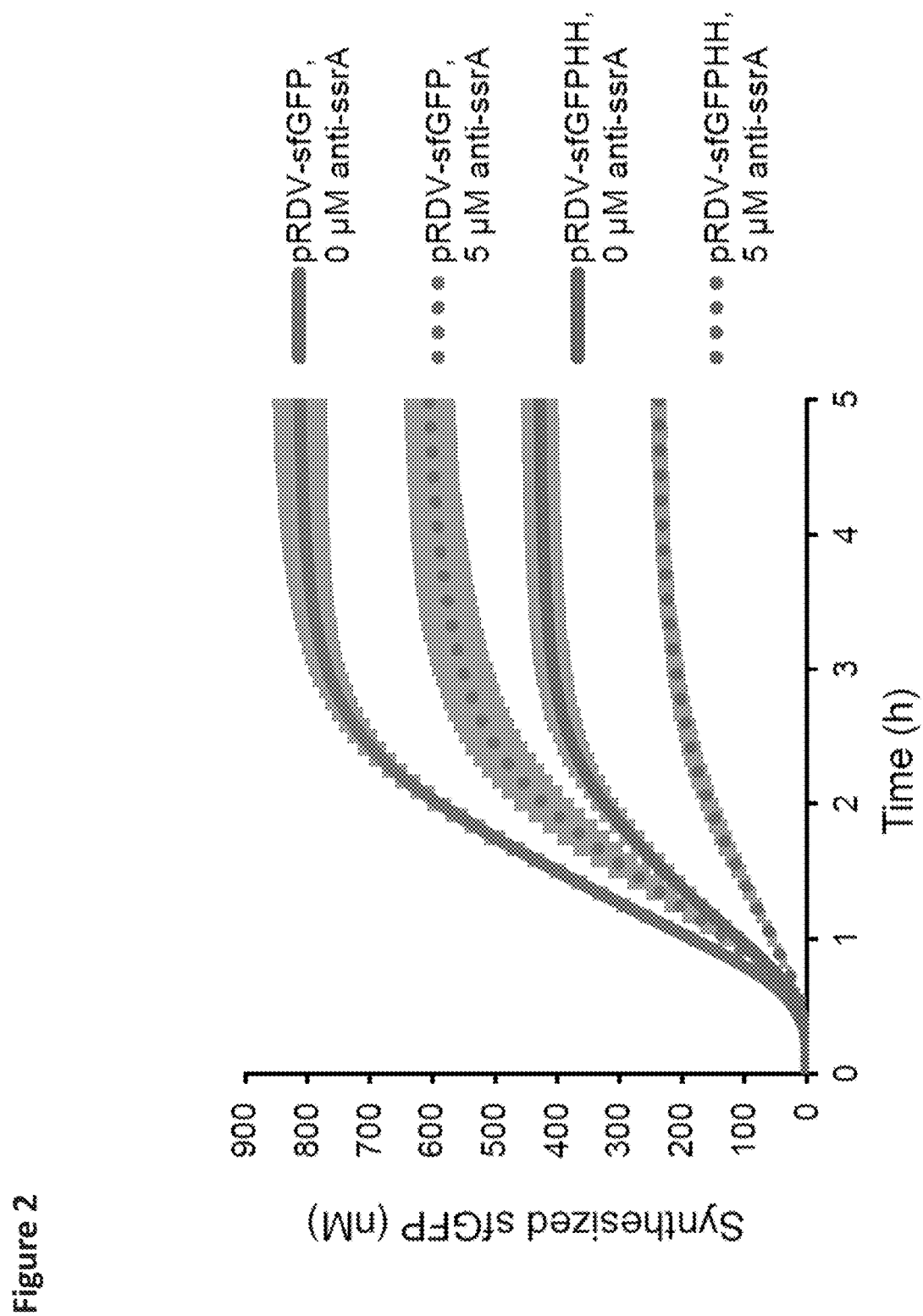
FIG. 2. iSAT translation of sfGFP and sfGFPHH from pRDV vectors, with 0 or 5 μM anti-ssrA oligonucleotide. iSAT reactions were performed with pRDV vectors containing the gene for sfGFP along with the TolA spacer. Constructs were made with (red) or without (blue) a 3' HH ribozyme for processing of transcribed mRNA. Solid lines represent reactions with 0 μM anti-ssrA oligonucleotide and dotted lines represent 5 μM anti-ssrA oligonucleotide. Values represent averages of three independent reactions and shading represents one standard deviation (s.d.).

To test this approach, we inserted the gene for superfolder green fluorescent protein (sfGFP) upstream of the spacer sequence. When used in iSAT reactions, this approach should generate one sfGFP molecule for each translating ribosome, and those ribosomes should stall at the 3' end of the mRNA due to stop codon removal. In our iSAT reactions, we compared translation from our pRDV-sfGFPHH construct against a similar construct lacking the hammerhead ribozyme (pRDV-sfGFP) and monitored green fluorescence over time, with and without 5 µM anti-ssrA oligonucleotide to block the native stalled ribosome dissociation mechanism likely found in our crude extract (FIG. 2). Translation in all reactions appears to slow abruptly at 2.5 h, but the level of translation is significantly altered by both the HH element and the anti-ssrA oligonucleotide. Use of pRDV-sfGFPHH in place of pRDV-sfGFP or addition of the oligonucleotide results in a large decrease in sfGFP production. The combination of these components results in 236 nM sfGFP production. Since iSAT reactions use 300 nM r-proteins (TP70), 300 nM sfGFP is the theoretical maximum production if one sfGFP molecule is properly displayed by each ribosome.

To ensure proper stalling of ribosomes after sfGFP synthesis, we performed sedimentation analysis of iSAT reactions for fluorescence analysis of gradient fractions. Sedimentation analysis involves the ultracentrifugation of iSAT reactions through a sucrose gradient to separate ribosomal particles based on size and density in order to visualize assembly of ribosomes and ribosomal subunits. By measuring the fluorescence of gradient fractions, we can determine if sfGFP is associating with stalled 70S ribosomes or is merely free in solution. 70S ribosomes have been shown to equilibrate at 11 to 13 mL into the 19 mL SW32.1 gradients (21).

Figure 3:
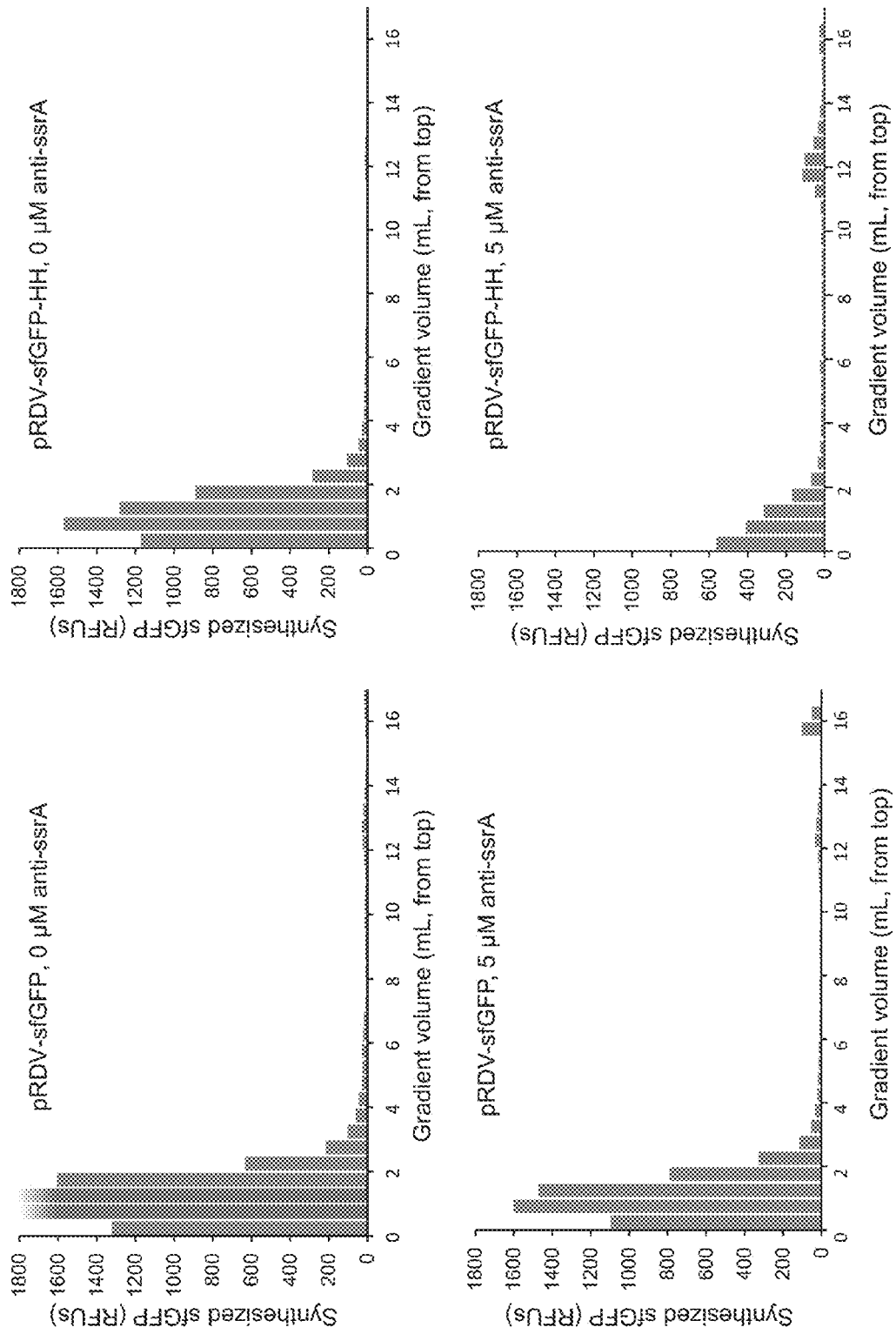
FIG. 3. Fluorescence sedimentation analysis of iSAT reactions with pRDV-sfGFP or sfGFPHH, with 0 or 5 μM anti-ssrA oligonucleotide. iSAT reactions contained (A) pRDV-sfGFP with 0 μM anti-ssrA, (B) pRDV-sfGFPHH with 0 μM anti-ssrA, (C) pRDV-sfGFP with 5 μM anti-ssrA, or (D) pRDV-sfGFPHH with 5 μM anti-ssrA. Samples were fractionated every 500 μL starting from the top of the gradient, and fluorescence of each fraction was measured. Values represent relative fluorescence units (RFUs) above background reactions without sfGFP translation. Note that the second and third fractions in exceed the axis limit (2557 and 2830 RFUs, respectively).

In FIG. 3, the reaction with the HH construct and anti-ssrA oligonucleotide (FIG. 3D) shows an increase in fluorescence at 11 to 13 mL relative to the other reactions, indicating that both the hammerhead ribozyme and anti-ssrA oligonucleotide are required for iSAT ribosome display. Even with these components, only a small fraction of sfGFP appears at 11 to 13 mL, suggesting either inefficient stalling of the ribosome or release of sfGFP during sedimentation analysis. However, without these alterations to iSAT reactions, the fluorescence appears near the top of the gradient, indicating full release of sfGFP after translation.

Optimization of RISE Selection Conditions.

Figure 4:
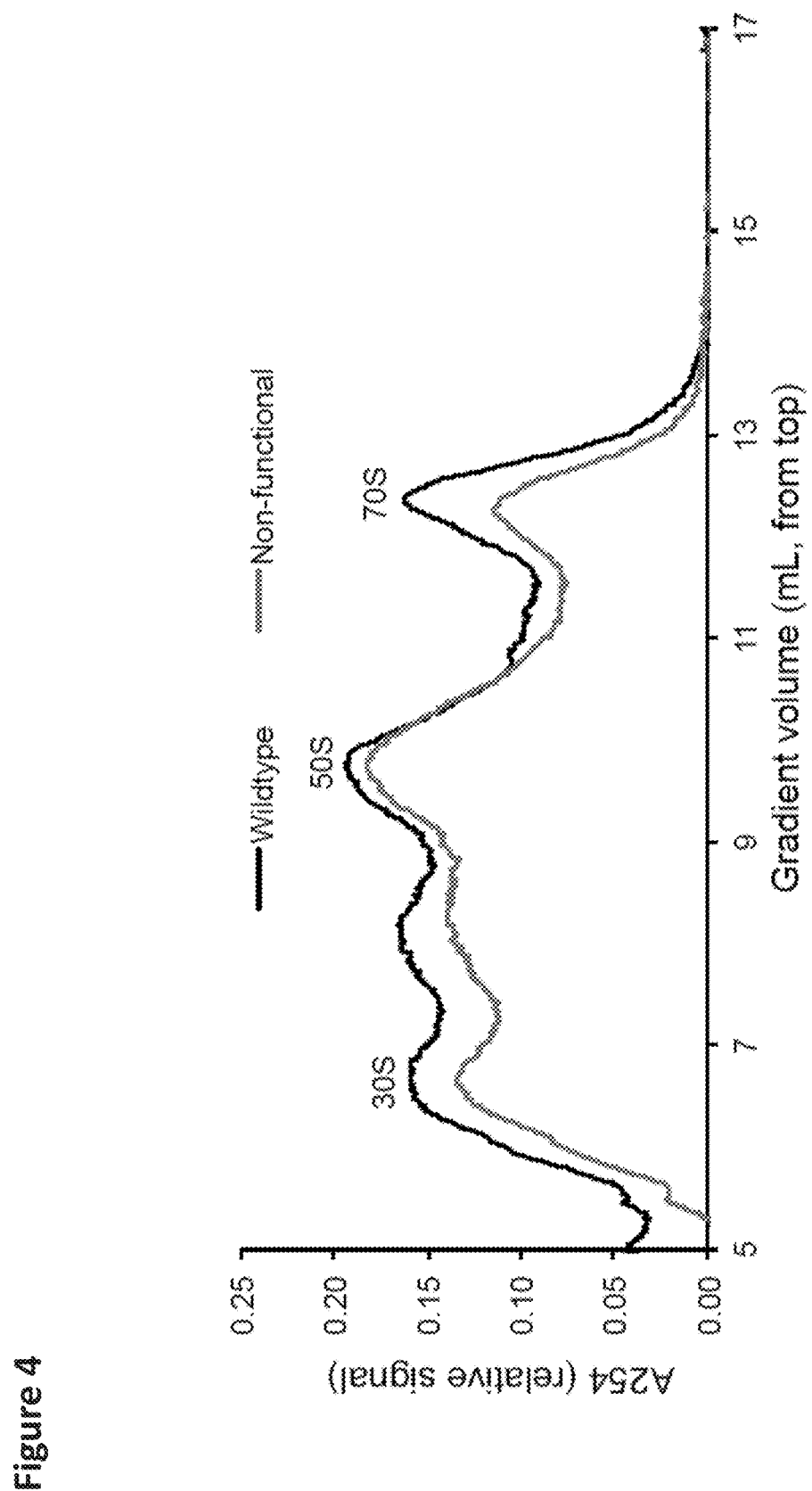
FIG. 4. Sedimentation analysis of iSAT reactions with wild type or non-functional rRNA operon. Peak identities are labeled.

For ribosome display selection to be efficient, conditions must be determined that allow for selection of targets of interest with high specificity over other library members. In the case of RISE, we developed an assay to distinguish selective capture of tags translated by functional ribosomes versus capture of rRNA through non-specific interactions of nucleic acids or ribosomal proteins. We chose to run parallel iSAT reactions with functional, wild type rRNA operon plasmids or non-functional rRNA operon plasmids that included lethal point mutations in both the 16S and 23S rRNA (ΔC967 and G2252A, respectively). To validate this approach, we used sedimentation analysis to show that non-functional rRNA still formed native-like ribosomal particles to preserve non-specific interactions (FIG. 4). By comparing specific capture of functional iSAT ribosomes, and non-specific capture of non-functional iSAT ribosomes, as determined by qPCR for 23S rRNA, we can assess the relative specificity of selective tags and selection conditions for functional ribosomes over non-specific binding of ribosomes or ribosomal components.

As an initial experiment, we tested the use of anti-FLAG M2 magnetic beads (Sigma) for isolation of iSAT ribosomes displaying a FLAG-tag. We developed a preliminary RISE protocol for FLAG-tag expression and capture using wash buffers and conditions suggested by the magnetic bead product literature and reported for ribosome display by Zahnd et al. (48). The first variable of concern was the time of the iSAT reaction, as ribosome display complexes are typically most stable after translation reaction times of 6 to 10 min (50). However, in FIG. 2, we observed that iSAT reactions require approximately 30 min for rRNA synthesis, ribosome assembly, and translation of detectable levels of displayed sfGFP. While the FLAG-tag should be translated and displayed more quickly than sfGFP, there is a lag time associated with iSAT reactions that had to be taken into account.

Figure 5:
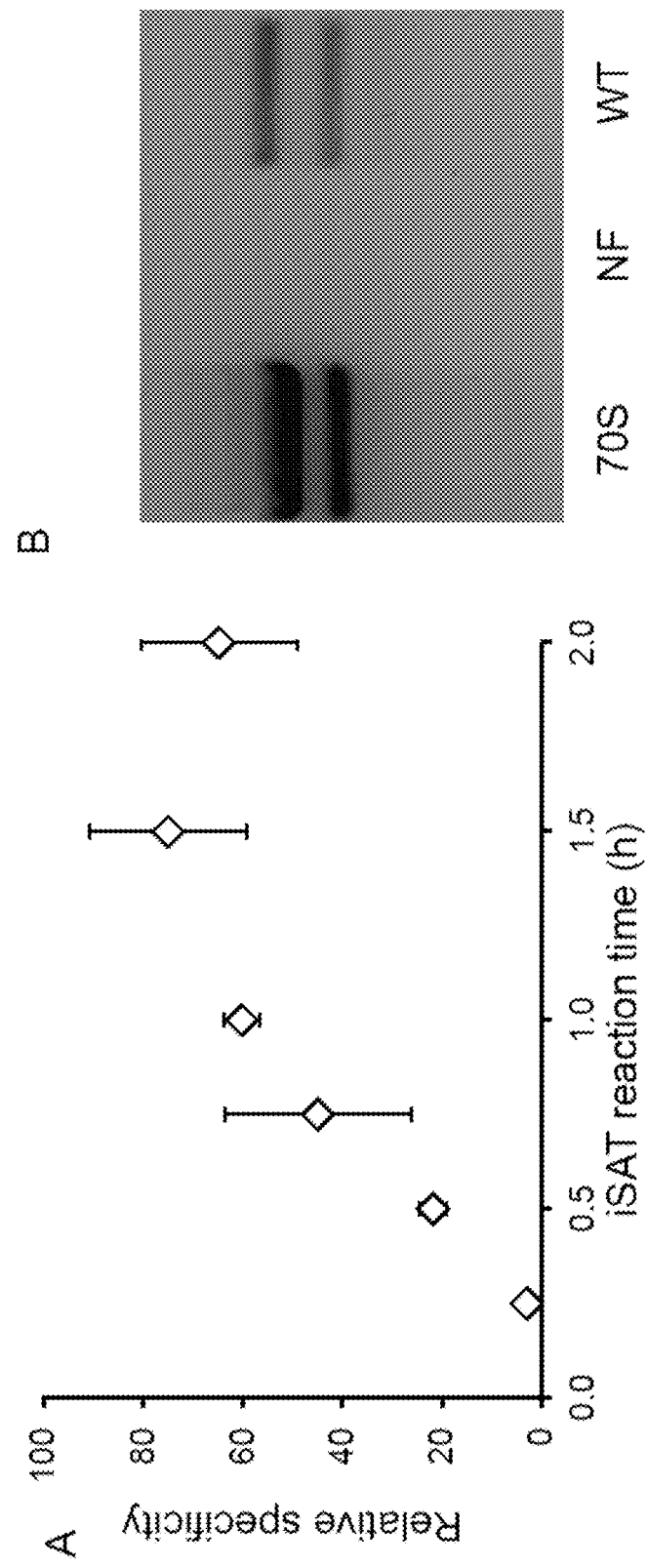
FIG. 5. Capture of ribosomes through ribosome display with FLAG-tag. (A) Relative specificity of capture by anti-FLAG magnetic beads for iSAT reactions displaying FLAG-tag. Reactions were incubated from 15 min to 2 h. Values represent averages of three independent pairs of reactions and error bars represent one s.d. (B) Agarose gel showing ribosomes captured from iSAT reactions with non-functional (NF) or wild type (WT) rRNA operon incubated for 1.5 h at 37° C. 4.5 pmol purified 70S ribosomes were run for comparison to represent the maximum theoretical number of iSAT ribosomes for 300 nM ribosomal proteins in a 15 μL reaction. Top band represents 23S rRNA and bottom band represents 16S rRNA.

In varying reaction time, we observed that relative specificity of functional ribosome capture is highest for 1.5 h iSAT reactions (where relative specificity is the amount of captured ribosomes from iSAT reactions with functional rRNA operon plasmid relative to the amount of captured ribosomes from iSAT reactions with non-functional rRNA operon plasmid) (FIG. 5A). Visualization of the recovered nucleic acids from the 1.5 h reactions shows that reactions with non-functional rRNA operon plasmids do not show visible rRNA capture, where as reactions with functional wild type rRNA operon plasmids show bands representative of 23S and 16S rRNA (FIG. 5B).

Figure 6:
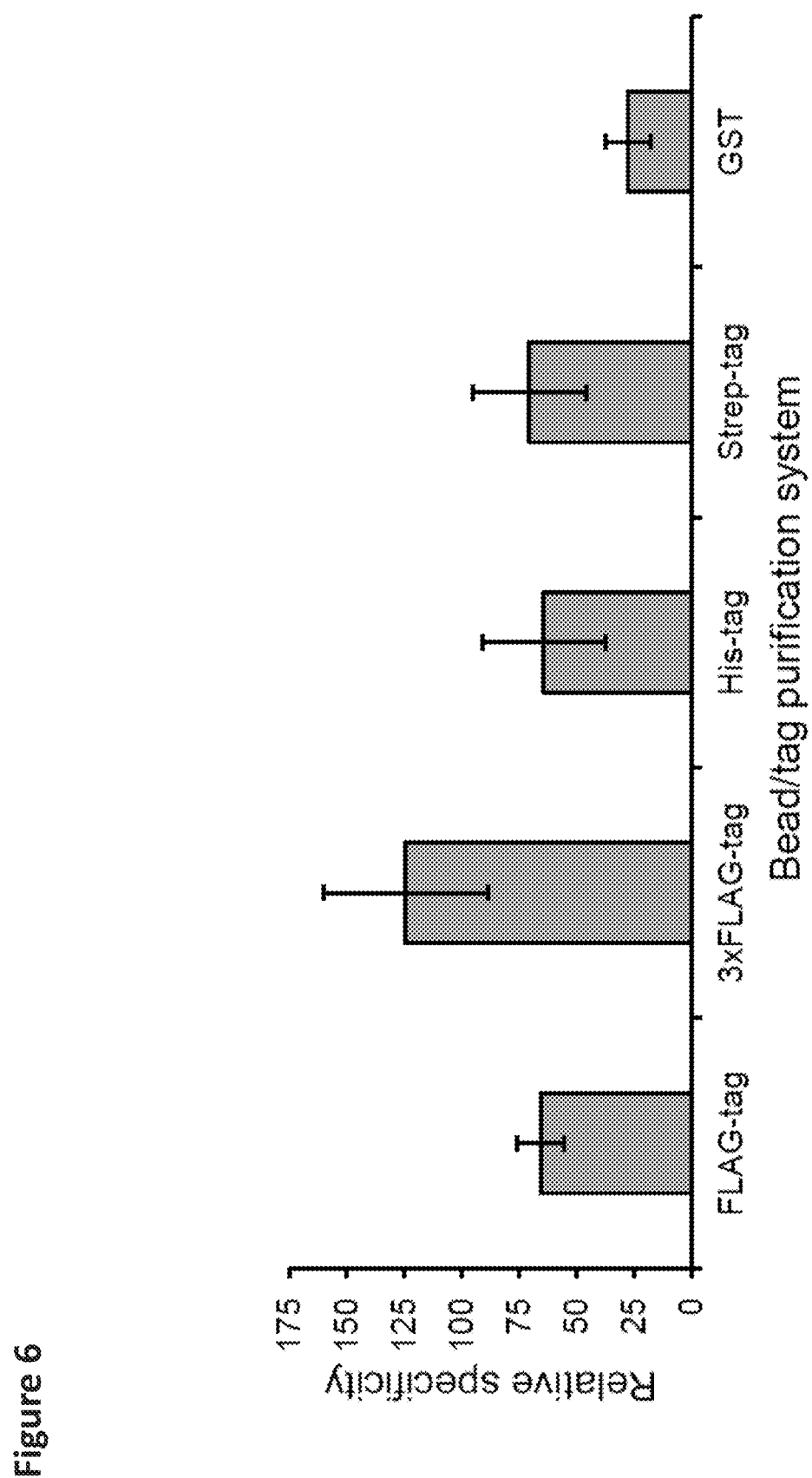
FIG. 6. Comparison of relative specificity of various bead/tag purification systems for use in RISE. Wash methods were held constant for comparison. Values represent averages of three independent pairs of reactions and error bars represent one s.d.

To choose a selective tag for RISE, we screened several common selective peptide tags that had commercially-available magnetic capture beads, as this would allow for high-throughput, bench-scale experiments for optimizing conditions. The genes for each tag (FLAG-tag, 3×FLAG-tag, His-tag, Strep-tag, and glutionine S-transferase (GST)) were inserted into the pRDV-HH vector. iSAT reactions expressing each tag or protein were incubated for 1.5 h, except for GST, which was incubated for 2 h to account for the additional translation and folding times associated with expressing a larger selective protein. Binding and wash conditions were held constant for all bead/tag combinations, even though each combination would require condition optimization to achieve maximum specificity. From this screen, we observed that the 3×FLAG-tag peptide, a tag built from three copies of the traditional FLAG-tag, provided the most promising results, with 124-fold specificity for functional ribosomes (FIG. 6). The 3×FLAG peptide provided a strong starting point for optimizing reaction conditions.

Figure 7:
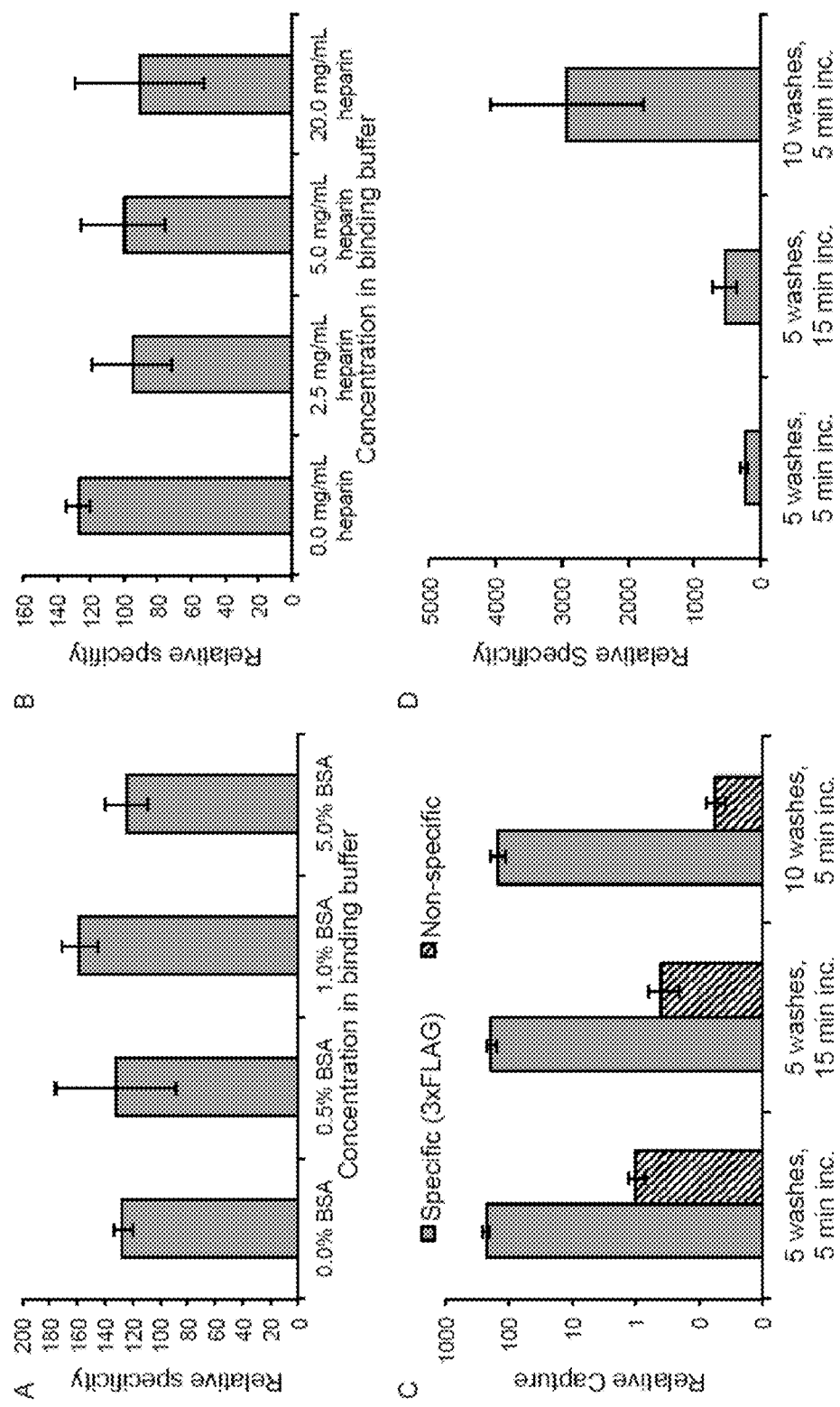
FIG. 7. Optimization of binding and wash buffers for RISE using 3×FLAG-tag. For the binding buffer, additives (A) BSA (% w/v) and (B) heparin were tested. For wash conditions, the number of washes and incubation of each wash were varied: (C) relative capture of iSAT ribosomes from specific capture (functional ribosomes) and non-specific capture (non-functional ribosomes) and (D) relative specificity of each wash condition. Values represent averages of three independent pairs of reactions and error bar represent one s.d.

Using the 3×FLAG-tag and anti-FLAG magnetic beads, we next optimized binding and wash conditions. The adjustment of blocking additives and wash buffers provided modest improvements (FIG. 7, Table 1).

TABLE 1

Optimization of NaCl and Tween-20 concentration in wash buffer RISE method with 3xFLAG-tag.

| Specificity using various wash buffers | Tween-20 (%) | | | |
|---|---|---|---|---|
| | 0.05 | 0.25 | 1.00 | 5.00 |
| NaCl (M)  0.15 | 126 | 150 | 129 | 119 |
| 0.30 | 118 | 110 | 87 | 89 |
| 0.50 | 92 | 93 | 101 | 85 |
| 1.00 | 85 | 94 | 71 | 84 |

Bovine serum albumin (BSA) in the binding buffer provided a 25% improvement in relative specificity when used at 1.0% w/v, while addition of heparin in the binding buffer decreased relative specific, so it was removed from the protocol (FIGS. 7A and 7B). Meanwhile, altering the Tween® 20 concentrations from 0.05% w/v to 0.25% w/v produced a modest improvement in relative specificity of 19% (Table 1). Most importantly, though, we found that the specificity was greatly improved by increasing the stringency of the washing steps, either by increasing the incubation time of each wash step from 5 to 15 minutes or, more significantly, by increasing the number of washes from 5 to 10 washes (FIGS. 7C and 7D). While we observed that specific capture is unchanged by increased wash stringency, non-specific capture was significantly lowered, resulting in relative specificity of >1,000-fold (FIG. 7C).

To complete RISE, we needed to develop a method to recover isolated rRNA sequences in the form of DNA, and reinsert recovered DNA into the rRNA operon plasmid. We sought to assemble DNA in vitro to avoid inefficiencies in cellular transformation and potential bias of cells for or against particular DNA sequences. After trial and error using a variety of DNA assembly methods, including circular polymerase extension cloning (CPEC) (51), Gibson Assembly (52), and Golden Gate Assembly (53), we found that digestion using off-site type Hs restriction enzymes and quick ligation yielded the best results.

Figure 8:
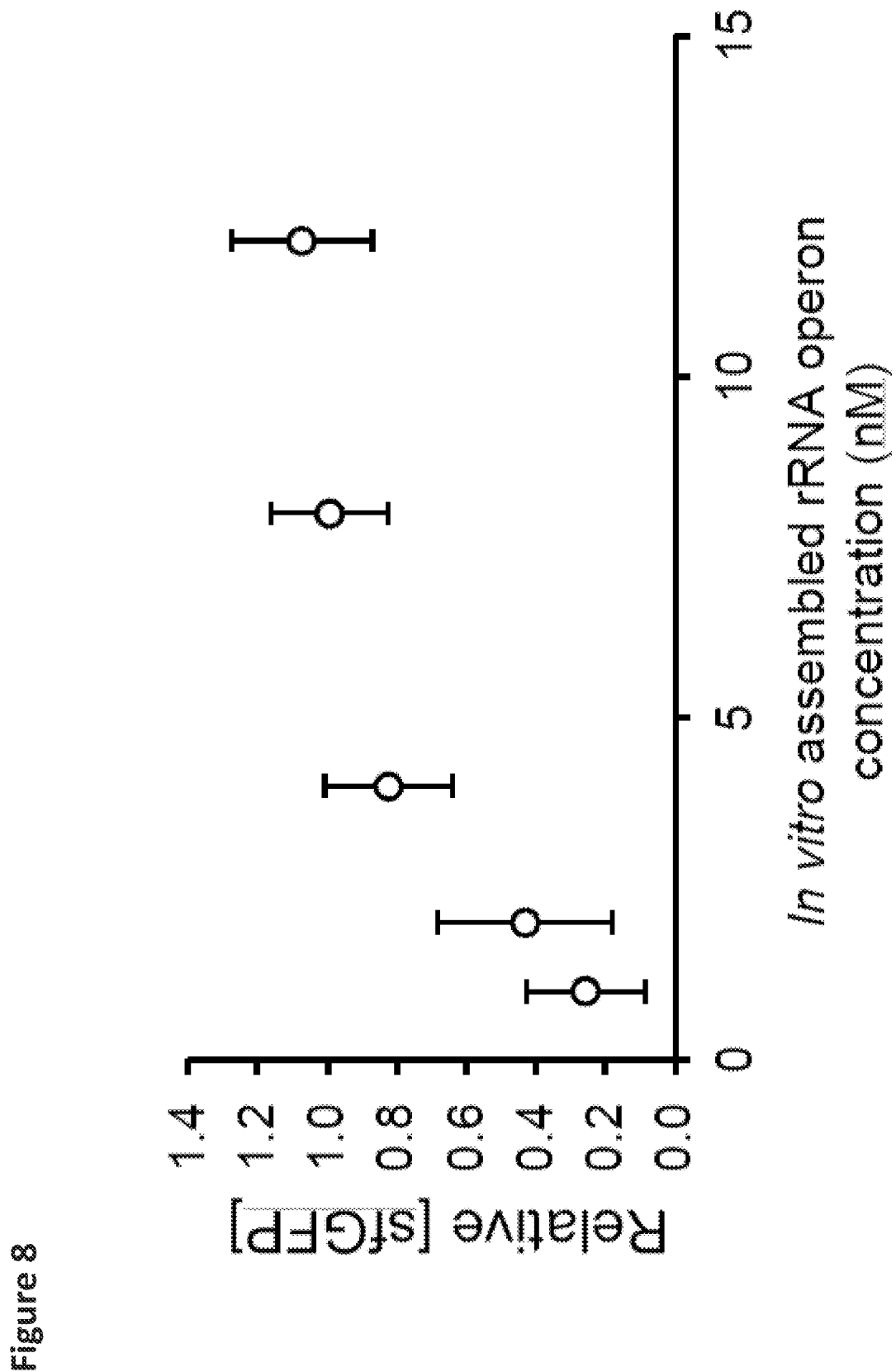
FIG. 8. iSAT reaction activity from in vitro assembled rRNA operon. rRNA operon plasmid was assembled in vitro from a 660 bp fragment of 23S rRNA and the pT7rrnBΔ660. Reporter plasmid, pY71sfGFP, was included at 1 nM. Values represent averages of three independent reactions and error bars represent one s.d.

Since the first three libraries of interest included mutations of 23S rRNA within a small region (see below), we decided on a 660 bp fragment for the 23S rRNA gene (bases 1962 to 2575) as the target for RT-PCR and in vitro rRNA operon assembly. As a pilot experiment, we amplified the 660 bp fragment from the native 23S rRNA gene and assembled it with pT7rrnBΔ660, an rRNA operon plasmid lacking those 660 bp of the 23S rRNA gene. This approach yielded plasmid that required 8-fold excess of DNA to achieve the same iSAT activity as the original pT7rrnB plasmid (FIG. 8). While this suggests that only ~12% of the plasmids are properly assembled, this is an acceptable approach for RISE.

Ribosomal Peptidyl Transferase Center.

As an initial test of RISE, we chose to look at base mutations in the peptidyl transferase center (PTC) of the ribosome. The PTC is made of the 23S rRNA, and research has identified a region of 79 bases within the PTC that contain six post-transcriptionally-modified bases (2445, 2449, 2457, 2498, 2503, and 2504) that are required for ribosome activity (32). To explore the effect of mutations in this region, we created two libraries of rRNA operon plasmids, with one library, termed 6E, consisting of degenerate mutations to the six essential post-transcriptionally-modified bases of 23S rRNA (32). The other library, termed 12NC, consisted of degenerate mutations to 12 bases of the critical region of the 23S rRNA PTC that are not conserved between the bacterial species *E. coli*, *Bacillus stearothermophilus*, and *Thermus aquaticus*: 2461, 2462, 2464, 2468, 2471, 2474, 2477, 2479, 2482, 2486, 2488, and 2489. This analysis is consistent with data from the Comparative RNA Web Site (54). The 6E and 12NC libraries theoretically contained 4,096 ($4^6$) and $1.7 \times 10^7$ ($4^{12}$) members, respectively.

Figure 9:
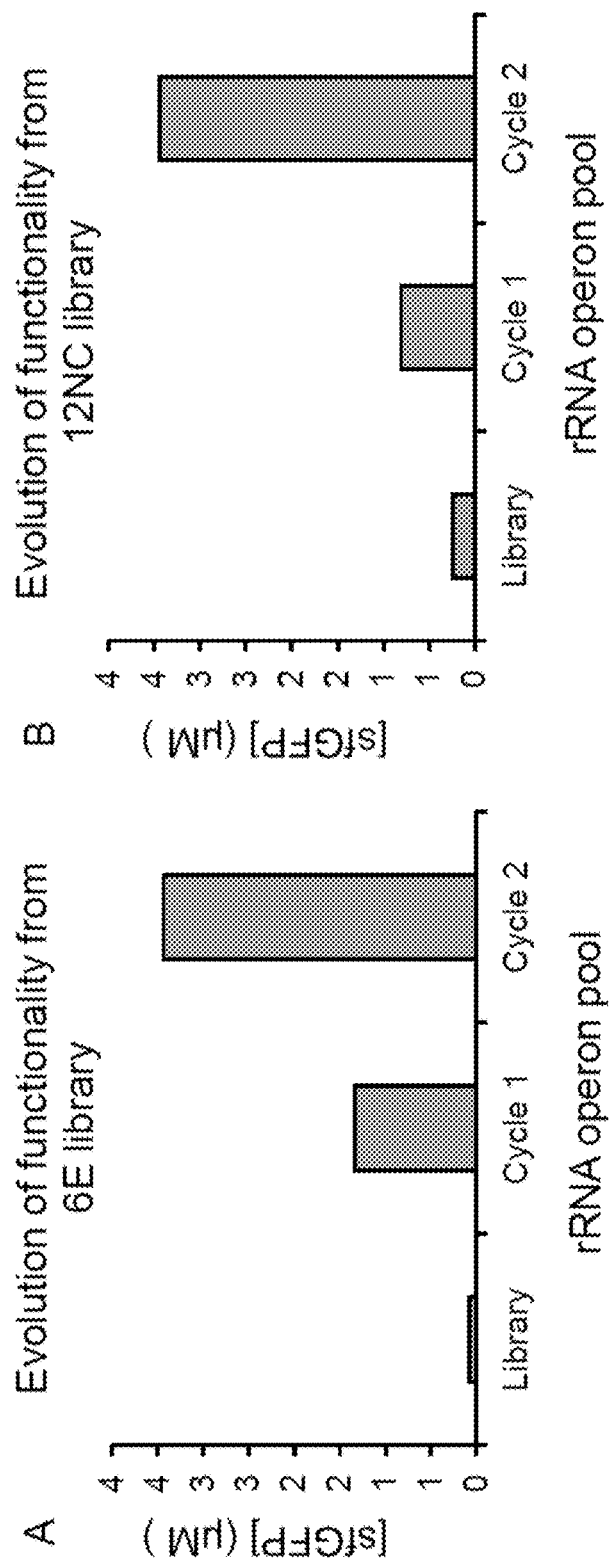
FIG. 9. sfGFP production of iSAT reactions using rRNA operon pools for (A) 6E and (B) 12NC evolutions, with pools including original libraries and 1 or 2 RISE cycles. Values represent averages of two independent reactions.

RISE was applied under normal iSAT reaction conditions to these libraries over two cycles. The initial libraries and operon pools created from recovered rRNA after each cycle were tested for activity in iSAT reactions and sent for sequencing. The activity tests show an increase in protein synthesis from rRNA operon reassembled after each RISE cycle (FIG. 9). Meanwhile, the sequence traces of the initial libraries show proper degeneracy of the 6 bases of the 6E library or the 12 bases of the 12NC library, and both libraries show convergence towards the native sequence after just one RISE cycle, with nearly complete convergence after two RISE cycles (data not shown). The size of the 12NC library and rapid convergence after two RISE cycles suggests an approximately 4,000-fold specificity for RISE in practice.

Evolution of Clindamycin-Resistant Ribosomes.

To demonstrate RISE for evolution of ribosomes with new functionality, we sought to recreate the evolution of clindamycin-resistant ribosomes from Cochella and Green (2004) in which ribosome libraries were constructed in vivo, purified, and used for in vitro ribosome display, with each cycle requiring a round of transformation, cell growth, and ribosome purification (18). First, we mutated 6 bases of 23S rRNA, 2057 to 2062, that are associated with clindamycin binding (55). We then applied RISE to the clindamycin-resistance (CR) library with either 0 or 500 µM clindamycin in the iSAT reaction. After each RISE cycle, we analyzed the composition of the rRNA operon pools through sequencing (data not shown). As with the 6E and 12NC library constructions, we observed that the CR library showed degeneracy at the 6 mutated bases. After three RISE cycles, the 0 µM clindamycin treatment resulted in rRNA operon pools mostly converging to the wild type sequence. However, the 500 µM clindamycin treatment showed convergence at bases 2060 and 2061, but high degeneracy at the other bases.

Since the rRNA sequences from the CR library had not converged, we transformed the rRNA operon pools after 3 RISE cycles and purified and sequenced DNA encoding 23S rRNA from individual colonies (data not shown). For the 0 µM clindamycin treatment, 13 of 26 sequences contained the wild type sequence, and the other 13 sequences were each unique. However, for the 500 µM clindamycin treatment, no wild type sequences were observed from 19 sequences. Additionally, the 19 sequences resulted in 18 unique sequences, showing no convergence except for bases 2060 and 2061.

Figure 10:
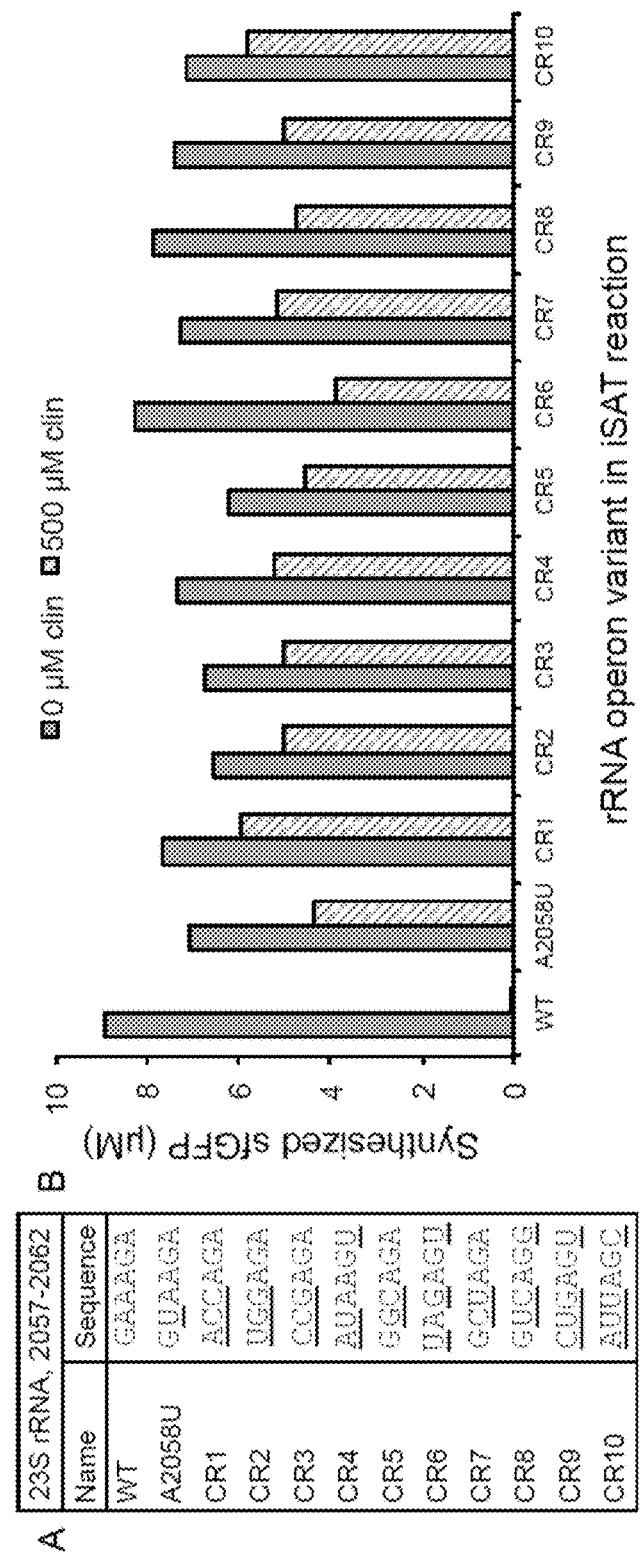
FIG. 10. Sequences and activity of individual rRNA operon variants recovered from clindamycin-resistance evolution using RISE. (A) Table of individual variants tested in iSAT reactions. Sequences CR1 through CR10 were isolated plasmids obtained after three RISE cycles for clindamycin-resistance evolution. (B) sfGFP production of iSAT reactions using 1 nM purified plasmid from individual rRNA operon variants. Values represent averages of two independent reactions.

From the 500 µM clindamycin-resistance evolution, we purified plasmids from 10 colonies and tested their activity in iSAT reactions with and without clindamycin (FIG. 10). All 10 colonies showed significant resistance to 500 µM clindamycin, despite a variety of sequences being represented.

Discussion

Development of RISE required coupling the iSAT system for in vitro ribosome construction with the methods associated with ribosome display. Based on the current 15 µL scale, iSAT reactions utilize $9 \times 10^9$ DNA molecules of the rRNA operon plasmid. The capture of approximately $3 \times 10^{11}$ ribosomes by RISE provides full coverage of DNA used in the iSAT reaction, suggesting that the amount of operon DNA used in the reactions is currently limiting RISE library size to approximately $10^9$ molecules, or degeneracy of up to 15 bases. Development of an improved in vitro DNA assembly method could provide another order of magnitude to the library size, and scaling up the iSAT reaction could also increase the library size.

Additionally, variation of the ribosome display vector could further improve the system. Inserting the hammerhead ribozyme gene into the pRDV vector allowed for rapid experimentation and removed the need for large scale mRNA synthesis. The pRDV-HH vector appears to successfully stall the ribosome based on iSAT activity and sucrose gradient ribosome profiling (FIGS. 2 and 3), and its use in this study allowed for successful selection of functional ribosomes. Further improvement of the construct could be achieved through optimization of the spacer sequence length or through introduction of other stalling mechanisms, such as SecM (35,56,57). For our purposes, however, pRDV-HH is sufficient for high specificity of functional ribosome capture.

Similarly, while RISE was developed for high specificity for functional ribosomes, there are a variety of conditions that can be further manipulated. Different wash buffers or other blocking additives could be tested, or conditions could be altered improve the use of other selective tags with different properties. One example would be the use of a selective protein, such as glutathione-S-transferase (GST), in place of a selective peptide to put an additional burden of translation on the ribosome, which may allow for improved specificity for highly active ribosomes over weakly active ribosomes. However, this modification would require optimization GST folding conditions within the iSAT reaction and subsequent binding steps. Likewise, conditions such as iSAT reaction time could be adjusted to be more or less stringent to alter the specificity of RISE.

The results from evolving the 6E and 12NC libraries both resulted in convergence of the libraries to wild type sequences. This was not surprising for the 6E library, as the bases were shown to be essential and require post-transcriptional modifications to form functional ribosomes (32). However, the rapid convergence of the 12NC library was unexpected, as we chose this library thinking it would result in several viable sequences and demonstrate the ability of RISE to uncover novel mutations. Instead, it demonstrated the high specificity of RISE, with estimates of >1,000-fold specificity being validated by this result. These results suggest that the 12 particular bases within the peptidyl transferase center of the *E. coli* ribosome may not be amenable to mutations. However, viable mutations of other 23S bases within the critical region of 23S rRNA have been identified (58).

Finally, we demonstrated that RISE was applicable to ribosome engineering efforts through the evolution of clindamycin-resistant ribosomes. The efficiency of RISE compares favorably to previous work with in vivo constructed ribosome libraries that required ribosome purifications and six cycles of evolution (18). After three RISE cycles using 500 µM clindamycin, ten rRNA operon variants were isolated that showed greater than 47% activity in iSAT reactions in the presence of 500 µM clindamycin relative to their activity without clindamycin. The ten isolated variants contained two, three, or four bases mutations from among six bases. This result demonstrates that ability of RISE to uncover novel combinations of bases that may not be accessible using other methods.

Overall, RISE is an exciting new approach to exploring ribosomal mutations that removes the restrictions of cell viability and transformation efficiency encountered by in vivo studies. With this new approach, ribosomal mutants can be rapidly created and screened, providing a powerful new tool to biologists and bioengineers alike. Moving forward, we anticipate using RISE to probe the *E. coli* ribosome for mutatable regions, to determine which ribosomal structures can be deleted while preserving ribosome functionality, and to introduce mutations that favor unnatural amino acid incorporation.

REFERENCES

1. Bremer, H. and Dennis, P. P. (1996) Modulation of Chemical Composition and Other Parameters of the Cell by Growth Rate. In Neidhardt, F. C., Curtiss III, R., Ingraham, J. L., Lin, E. C. C., Low, K. B., Magasanik, B., Reznikoff, W. S. and Riley, M. (eds.), *Escherichia coli and Salmonella*: Cellular and Molecular Biology. 2nd ed. American Society for Microbiology, Washington, D.C., pp. 1553-1569.
2. Parker, J. (1989) Errors and alternatives in reading the universal genetic code. Microbiol. Rev., 53, 273-298.

3. Baneyx, F. (1999) Recombinant protein expression in *Escherichia coli*. Curr. Opin. Biotechnol., 10, 411-421.
4. Chou, C. P. (2007) Engineering cell physiology to enhance recombinant protein production in *Escherichia coli*. Appl. Microbiol. Biotechnol., 76, 521-532.
5. Sorensen, H. P. and Mortensen, K. K. (2005) Advanced genetic strategies for recombinant protein expression in *Escherichia coli*. J. Biotechnol., 115, 113-128.
6. Carlson, E. D., Gan, R., Hodgman, C. E. and Jewett, M. C. (2012) Cell-free protein synthesis: applications come of age. Biotechnol. Adv., 30, 1185-1194.
7. Hodgman, C. E. and Jewett, M. C. (2012) Cell-free synthetic biology: thinking outside the cell. Metab. Eng., 14, 261-269.
8. Jewett, M. C. and Swartz, J. R. (2004) Mimicking the *Escherichia coli* cytoplasmic environment activates long-lived and efficient cell-free protein synthesis. Biotechnol. Bioeng., 86, 19-26.
9. Katzen, F., Chang, G. and Kudlicki, W. (2005) The past, present and future of cell-free protein synthesis. Trends Biotechnol., 23, 150-156.
10. Kim, D. M., Kigawa, T., Choi, C. Y. and Yokoyama, S. (1996) A highly efficient cell-free protein synthesis system from *Escherichia coli*. Eur. J. Biochem., 239, 881-886.
11. Ohta, A., Yamagishi, Y. and Suga, H. (2008) Synthesis of biopolymers using genetic code reprogramming Curr. Opin. Chem. Biol., 12, 159-167.
12. Wang, K., Neumann, H., Peak-Chew, S. Y. and Chin, J. W. (2007) Evolved orthogonal ribosomes enhance the efficiency of synthetic genetic code expansion. Nat. Biotechnol., 25, 770-777.
13. Neumann, H., Wang, K., Davis, L., Garcia-Alai, M. and Chin, J. W. (2010) Encoding multiple unnatural amino acids via evolution of a quadruplet-decoding ribosome. Nature, 464, 441-444.
14. Hui, A. and de Boer, H. A. (1987) Specialized ribosome system: preferential translation of a single mRNA species by a subpopulation of mutated ribosomes in *Escherichia coli*. Proc. Natl. Acad. Sci. U.S.A, 84, 4762-4766.
15. Rackham, O. and Chin, J. W. (2005) A network of orthogonal ribosome×mRNA pairs. Nat. Chem. Biol., 1, 159-166.
16. Rackham, O. and Chin, J. W. (2005) Cellular logic with orthogonal ribosomes. J. Am. Chem. Soc., 127, 17584-17585.
17. Lee, K., Varma, S., SantaLucia, J., Jr. and Cunningham, P. R. (1997) In vivo determination of RNA structure-function relationships: analysis of the 790 loop in ribosomal RNA. J. Mol. Biol., 269, 732-743.
18. Cochella, L. and Green, R. (2004) Isolation of antibiotic resistance mutations in the rRNA by using an in vitro selection system. Proc. Natl. Acad. Sci. U.S.A., 101, 3786-3791.
19. Youngman, E. M. and Green, R. (2005) Affinity purification of in vivo-assembled ribosomes for in vitro biochemical analysis. Methods, 36, 305-312.
20. Terasaka, N., Hayashi, G., Katoh, T. and Suga, H. (2014) An orthogonal ribosome-tRNA pair via engineering of the peptidyl transferase center. Nat. Chem. Biol., 10, 555-557.
21. Fritz, B. R., Jamil, O. K. and Jewett, M. C. (2014) Implications of macromolecular crowding and reducing conditions for in vitro ribosome construction. In preparation.
22. Fritz, B. R. and Jewett, M. C. (2014) The impact of transcriptional tuning on in vitro integrated rRNA transcription and ribosome construction. Nucleic Acids Res., 42, 6774-6785.
23. Jewett, M. C., Fritz, B. R., Timmerman, L. E. and Church, G. M. (2013) In vitro integration of ribosomal RNA synthesis, ribosome assembly, and translation. Mol. Syst. Biol., 9, 678.
24. Liu, Y., Fritz, B. R., Anderson, M. J., Schoborg, J. A. and Jewett, M. C. (2014) Characterizing and Alleviating Substrate Limitations for Improved in vitro Ribosome Construction. ACS Synth. Biol.
25. Mizushima, S and Nomura, M. (1970) Assembly mapping of 30S ribosomal proteins from *E. coli*. Nature, 226, 1214.
26. Talkington, M. W., Siuzdak, G. and Williamson, J. R. (2005) An assembly landscape for the 30S ribosomal subunit. Nature, 438, 628-632.
27. Traub, P. and Nomura, M. (1968) Structure and function of *E. coli* ribosomes. V. Reconstitution of functionally active 30S ribosomal particles from RNA and proteins. Proc. Natl. Acad. Sci. U.S.A, 59, 777-784.
28. Green, R. and Noller, H. F. (1999) Reconstitution of functional 50S ribosomes from in vitro transcripts of *Bacillus stearothermophilus* 23S rRNA. Biochemistry, 38, 1772-1779.
29. Herold, M. and Nierhaus, K. H. (1987) Incorporation of six additional proteins to complete the assembly map of the 50 S subunit from *Escherichia coli* ribosomes. J. Biol. Chem., 262, 8826-8833.
30. Nierhaus, K. H. and Dohme, F. (1974) Total reconstitution of functionally active 50S ribosomal subunits from *Escherichia coli*. Proc. Natl. Acad. Sci. U.S.A, 71, 4713-4717.
31. Semrad, K. and Green, R. (2002) Osmolytes stimulate the reconstitution of functional 50S ribosomes from in vitro transcripts of *Escherichia coli* 23S rRNA. RNA, 8, 401-411.
32. Green, R. and Noller, H. F. (1996) In vitro complementation analysis localizes 23S rRNA posttranscriptional modifications that are required for *Escherichia coli* 50S ribosomal subunit assembly and function. RNA, 2, 1011-1021.
33. Hanes, J. and Pluckthun, A. (1997) In vitro selection and evolution of functional proteins by using ribosome display. Proc. Natl. Acad. Sci. U.S.A, 94, 4937-4942.
34. Roberts, R. W. (1999) Totally in vitro protein selection using mRNA-protein fusions and ribosome display. Curr. Opin. Chem. Biol., 3, 268-273.
35. Ohashi, H., Shimizu, Y., Ying, B. W. and Ueda, T. (2007) Efficient protein selection based on ribosome display system with purified components. Biochem. Biophys. Res. Commun., 352, 270-276.
36. Pluckthun, A. (2012) Ribosome display: a perspective. Methods Mol. Biol., 805, 3-28.
37. Keiler, K. C., Waller, P. R. and Sauer, R. T. (1996) Role of a peptide tagging system in degradation of proteins synthesized from damaged messenger RNA. Science, 271, 990-993.
38. Stemmer, W. P. (1994) DNA shuffling by random fragmentation and reassembly: in vitro recombination for molecular evolution. Proc. Natl. Acad. Sci. U.S.A., 91, 10747-10751.
39. Stemmer, W. P. (1994) Rapid evolution of a protein in vitro by DNA shuffling. Nature, 370, 389-391.
40. Cadwell, R. C. and Joyce, G. F. (1994) Mutagenic PCR. PCR Methods Appl., 3, S136-140.

41. Cirino, P. C., Mayer, K. M. and Umeno, D. (2003) Generating mutant libraries using error-prone PCR. Methods Mol. Biol., 231, 3-9.
42. Neylon, C. (2004) Chemical and biochemical strategies for the randomization of protein encoding DNA sequences: library construction methods for directed evolution. Nucleic Acids Res., 32, 1448-1459.
43. Hanes, J., Schaffitzel, C., Knappik, A. and Pluckthun, A. (2000) Picomolar affinity antibodies from a fully synthetic naive library selected and evolved by ribosome display. Nat. Biotechnol., 18, 1287-1292.
44. Lamla, T. and Erdmann, V. A. (2001) In vitro selection of other proteins than antibodies by means of ribosome display. FEBS Lett., 502, 35-40.
45. Matsuura, T. and Pluckthun, A. (2003) Selection based on the folding properties of proteins with ribosome display. FEBS Lett., 539, 24-28.
46. Takahashi, F., Ebihara, T., Mie, M., Yanagida, Y., Endo, Y., Kobatake, E. and Aizawa, M. (2002) Ribosome display for selection of active dihydrofolate reductase mutants using immobilized methotrexate on agarose beads. FEBS Lett., 514, 106-110.
47. Binz, H. K., Amstutz, P., Kohl, A., Stumpp, M. T., Briand, C., Forrer, P., Grutter, M. G. and Pluckthun, A. (2004) High-affinity binders selected from designed ankyrin repeat protein libraries. Nat. Biotechnol., 22, 575-582.
48. Zahnd, C., Amstutz, P. and Pluckthun, A. (2007) Ribosome display: selecting and evolving proteins in vitro that specifically bind to a target. Nat. Methods, 4, 269-279.
49. Rozen, S. and Skaletsky, H. (2000) Primer3 on the WWW for general users and for biologist programmers. Methods Mol. Biol., 132, 365-386.
50. Schaffitzel, C., Hanes, J., Jermutus, L. and Pluckthun, A. (1999) Ribosome display: an in vitro method for selection and evolution of antibodies from libraries. J. Immunol. Methods, 231, 119-135.
51. Quan, J. and Tian, J. (2009) Circular polymerase extension cloning of complex gene libraries and pathways. PLoS One, 4, e6441.
52. Gibson, D. G., Young, L., Chuang, R. Y., Venter, J. C., Hutchison, C. A., 3rd and Smith, H. O. (2009) Enzymatic assembly of DNA molecules up to several hundred kilobases. Nat. Methods, 6, 343-345.
53. Engler, C., Kandzia, R. and Marillonnet, S. (2008) A one pot, one step, precision cloning method with high throughput capability. PLoS One, 3, e3647.
54. Cannone, J. J., Subramanian, S., Schnare, M. N., Collett, J. R., D'Souza, L. M., Du, Y., Feng, B., Lin, N., Madabusi, L. V., Muller, K. M. et al. (2002) The comparative RNA web (CRW) site: an online database of comparative sequence and structure information for ribosomal, intron, and other RNAs. BMC Bioinf., 3, 2.
55. Schlunzen, F., Zarivach, R., Harms, J., Bashan, A., Tocilj, A., Albrecht, R., Yonath, A. and Franceschi, F. (2001) Structural basis for the interaction of antibiotics with the peptidyl transferase centre in eubacteria. Nature, 413, 814-821.
56. Evans, M. S., Ugrinov, K. G., Frese, M. A. and Clark, P. L. (2005) Homogeneous stalled ribosome nascent chain complexes produced in vivo or in vitro. Nat. Methods, 2, 757-762.
57. Nakatogawa, H. and Ito, K. (2002) The ribosomal exit tunnel functions as a discriminating gate. Cell, 108, 629-636.
58. Polacek, N., Gaynor, M., Yassin, A. and Mankin, A. S. (2001) Ribosomal peptidyl transferase can withstand mutations at the putative catalytic nucleotide. Nature, 411, 498-501.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

All methods described herein can be performed in any suitable order unless otherwise indicated herein or otherwise clearly contradicted by context. The use of any and all examples provided herein, is intended merely to better illuminate the invention and does not pose a limitation on the scope of the invention unless otherwise claimed. No language in the specification should be construed as indicating any non-claimed element as essential to the practice of the invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method of identifying an engineered or modified *E. coli* ribosome having functional activity under a defined condition, comprising:
   (a) performing an integrated ribosome synthesis assembly and translation (iSAT) reaction with a library of mutated rRNA templates and a ribosome display reporter template; and
   (b) partitioning a subpopulation of rRNAs in assembled mutated ribosomes having translational activity under the defined condition from a remainder population of mutated rRNAs present in the iSAT reaction; and
   (c) enriching the partitioned subpopulation of rRNAs in assembled mutated ribosomes having translational activity to identify the engineered *E. coli* ribosome having functional activity under the defined condition.

2. The method of claim 1, further comprising generating the library of mutated rRNA templates.

3. The method of claim 2, wherein the library of mutated rRNA templates is generated by a method that includes a step selected from the group consisting of DNA shuffling, error-prone DNA amplification, degenerate primer-based DNA amplification, and specific modifications based on crystal structure guided rational targeting.

4. The method of claim 1, wherein the ribosome display reporter template comprises a reporter gene operably linked to a 5'-promoter element, a 3'-spacer element, and a 3'-self-cleaving ribozyme element.

5. The method of claim 4, wherein the reporter gene comprises or encodes a binding partner.

6. The method of claim 5, wherein the partitioning step (b) comprises:
   (i) forming a ternary complex comprising a stalled ribosome on a mRNA terminated by a self-cleaving ribozyme in the presence of an anti-ssrA oligonucleotide; and
   (ii) selecting the ternary complex with a cognate binding partner to the binding partner of the reporter gene to form a quaternary complex comprising the ternary complex associated with the cognate binding partner.

7. The method of claim 6, wherein the cognate binding partner comprises a capture reagent.

8. The method of claim 6, wherein the binding partner comprises a peptide tag.

9. The method of claim 8, wherein the peptide tag is selected from a group consisting of FLAG-tag, 3×FLAG-tag, His-tag, Strep-tag, and glutathione S-transferase.

10. The method of claim 9, further comprising washing the selected quaternary complex under a defined stringency condition.

11. The method of claim 1, wherein the enriching step (c) comprises:
    (i) recovering the subpopulation of rRNAs in assembled mutated ribosomes having translational activity;
    (ii) converting the subpopulation of rRNAs to form a plurality of rRNA templates; and
    (iii) amplifying the plurality of rRNA templates.

12. The method of claim 1, wherein the defined condition is selected from the group consisting of defined temperature, defined pH, a redox environment, or the presence of one or more additives.

13. The method of claim 12, wherein the one or more additives comprise an antibiotic.

14. The method of claim 1, further comprising executing steps (a)-(c) in a reiterative manner.

15. A method of identifying an engineered or modified *E. coli* ribosome having functional activity in the presence of an antibiotic, the method comprising performing the method of claim 1 in the presence of the antibiotic.

* * * * *

SEQUENCE LISTING

```
<160> NUMBER OF SEQ ID NOS: 1

<210> SEQ ID NO 1
<211> LENGTH: 38
<212> TYPE: DNA
<213> ORGANISM: Escherichia coli

<400> SEQUENCE: 1
ttaagctgct aaagcgtagt tttcgtcgtt tgcgacta                              38
```